(12) United States Patent
Mosberg

(10) Patent No.: US 9,045,526 B2
(45) Date of Patent: Jun. 2, 2015

(54) COMPOUND AND METHOD FOR MODULATING OPIOID RECEPTOR ACTIVITY

(75) Inventor: Henry I. Mosberg, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 14/128,800

(22) PCT Filed: Jun. 22, 2012

(86) PCT No.: PCT/US2012/043819
§ 371 (c)(1),
(2), (4) Date: Dec. 23, 2013

(87) PCT Pub. No.: WO2012/178063
PCT Pub. Date: Dec. 27, 2012

(65) Prior Publication Data
US 2014/0154272 A1 Jun. 5, 2014

Related U.S. Application Data

(60) Provisional application No. 61/500,363, filed on Jun. 23, 2011.

(51) Int. Cl.
| A61K 38/00 | (2006.01) |
| A61P 23/00 | (2006.01) |
| C07K 5/107 | (2006.01) |
| C07K 7/06 | (2006.01) |
| A61K 38/07 | (2006.01) |
| A61K 45/06 | (2006.01) |

(52) U.S. Cl.
CPC .............. *C07K 5/1016* (2013.01); *A61K 38/00* (2013.01); *C07K 7/06* (2013.01); *A61K 38/07* (2013.01); *A61K 45/06* (2013.01)

(58) Field of Classification Search
None
See application file for complete search history.

(56) References Cited

U.S. PATENT DOCUMENTS

| 4,179,337 A | 12/1979 | Davis et al. |
| 4,301,144 A | 11/1981 | Iwashita et al. |
| 4,661,913 A | 4/1987 | Wu et al. |
| 4,670,417 A | 6/1987 | Iwasaki et al. |
| 4,791,192 A | 12/1988 | Nakagawa et al. |
| 5,216,124 A | 6/1993 | Hansen, Jr. et al. |
| 5,466,468 A | 11/1995 | Schneider et al. |
| 2008/0269143 A1 | 10/2008 | Lazarus et al. |

FOREIGN PATENT DOCUMENTS

| WO | WO-91/08759 A1 | 6/1991 |
| WO | WO-2010/071874 A2 | 6/2010 |

OTHER PUBLICATIONS

Arturrson et al., Correlation between oral drug absorption in humans and apparent drug permeability coefficients in human intestinal epithelial (Caco-2) cells. *Biochem. Biophys. Res. Commun.* 175(3): 880-5 (1991).

Balboni et al., Evaluation of the Dmt-Tic pharmacophore: conversion of a potent delta-opioid receptor antagonist into a potent delta agonist and ligands with mixed properties. *J. Med. Chem.* 45(3): 713-20 (2002).

Balboni et al., Potent delta-opioid receptor agonists containing the Dmt-Tic pharmacophore. *J. Med. Chem.* 45: 5556-63 (2002).

Balboni et al., Role of 2',6'-dimethyl-l-tyrosine (Dmt) in some opioid lead compounds. *Bioorg. Med. Chem.* 18(16): 6024-30 (2010).

Balboni et al., Synthesis and opioid activity of N,N-dimethyl-Dmt-Tic-NH-CH(R)-R' analogues: acquisition of potent delta antagonism. *Bioorg. Med. Chem.* 11: 5435-41 (2003).

Cechetto et al., Immunoelectron microscopy provides evidence that tumor necrosis factor receptor-associated protein 1 (TRAP-1) is a mitochondrial protein which also localizes at specific extramitochondrial sites. *Exp. Cell Res.* 260: 30-9 (2000).

Clapp et al., Cardiovascular and metabolic responses to two receptor-selective opioid agonists in pregnant sheep. *Am. J. Obstet. Gynecol.* 178(2): 397-401 (1998).

(Continued)

*Primary Examiner* — Thomas S Heard
(74) *Attorney, Agent, or Firm* — Marshall, Gerstein & Borun LLP

(57) ABSTRACT

The invention provides a compound of formula (I), wherein $R^1$ is H, C(NH)NH$_2$, an amino acid, or a peptide; X is OH, NH$_2$, NHR$^2$, NR$^2$R$^3$, an amino acid, or a peptide; $R^2$ and $R^3$ are selected from alkyl, alkylenearyl, or alkyleneheteroaryl; each $R^4$ and $R^5$ is independently H or CH$_3$; Z is 2-amino-2,3-dihydro-1H-indene-2-carboxylic acid; 2-amino-1,2,3,4-tetrahydronaphthalene-2-carboxylic acid; 6-amino-6,7,8,9-tetrahydro-5H-benzo[7]annulene 6-carboxylic acid; cyclohexylalanine; cyclohexylglycine; homophenylalanine; 1-naphthylalanine; 2-naphthylalanine; 1,2,3,4-tetrahydroisoquinoline-3-carboxylic acid; or octahydro-1H-indole-2-carboxylic acid; n is 0, 1, 2, 3, or 4; with the proviso that X is not NH$_2$ when $R^1$ is H, $R^4$ is H, $R^5$ is CH$_3$, Z is Aci, and n is 2; or a pharmaceutically acceptable salt, ester or solvate thereof. A method of treating pain and a method for treating a mu-opioid receptor mediated disorder and/or a delta-opioid receptor mediated disorder also are provided.

(I)

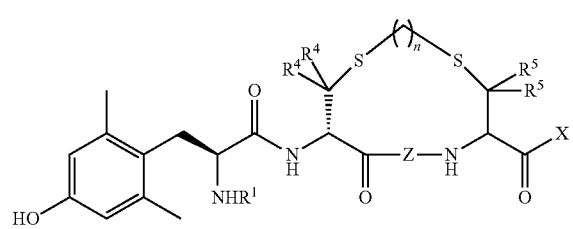

63 Claims, 6 Drawing Sheets

(56) References Cited

OTHER PUBLICATIONS

Clark et al., Endogenous RGS protein action modulates mu-opioid signaling through Galphao. Effects on adenylyl cyclase, extracellular signal-regulated kinases, and intracellular calcium pathways. *J. Biol. Chem.* 3278(11): 9418-25 (2003).

Davis et al., Preparation and characterization of antibodies with specificity for the amino-terminal tetrapeptide sequence of the platelet-derived connective tissue. Biochem. Intl. 10(3): 395-404 (1985).

Delcroix et al., Cell-penetrating peptides for antiviral drug development. *Pharmaceuticals*, 3(3): 448-70 (2010).

Hansen et al., Systemic analgesic activity and δ-opioid selectively in [2,6-dimethyl-Tyr1, D-Pen2, D-Pen5]enkephalin. *J. Med. Chem.* 35 (4): 684-7 (1992).

Harris et al., A simple microcomputer interface for tail-flick determination. *J. Pharmacol. Meth.* 20: 103-8 (1988).

Hubbell et al., Antagonism at delta opioid receptors blocks cocaine's, but not morphine's, enhancement of responding for intracranial stimulation. *Exp. Clin. Psychopharmacol.* 3(2): 123-8 (1995).

Husbands et al., BU74, a complex oripavine derivative with potent kappa opioid receptor agonism and delayed opioid antagonism. *Eur. J. Pharmacol.* 509(2-3): 117-25 (2005).

Jones et al., Blood-brain barrier transport of therapeutics via receptor-mediation. *Pharm. Res.* 24(9): 1759-71 (2007).

Jutkiewicz et al., The convulsive and electroencephalographic changes produced by nonpeptidic delta-opioid agonists in rats: comparison with pentylenetetrazol. *J. Pharmacol. Exp. Ther.* 317(3): 1337-48 (2006).

Koda et al., Synthesis and in vitro evaluation of a library of modified endomorphin 1 peptides. *Bioorgan. Med. Chem.*, 16(11): 6286-96 (2008).

Kosterlitz et al., Kinetic parameters of narcotic agonists and antagonists, with particular reference to N-allylnoroxymorphone (naloxone). *Br. J. Pharmacol. Chemother.* 33(2): 266-76 (1968).

Larsen et al., The Merrifield peptide synthesis studied by near-infrared Fourier-transform Raman spectroscopy. *J. Am. Chem. Soc.* 115: 6247-53 (1993).

Lazarus et al., Function of negative charge in the "address domain" of deltorphins. *J. Med Chem.* 34: 1350-9 (1991).

Lee et al., Differential binding properties of oripavines at cloned mu- and delta-opioid receptors. *Eur. J. Pharmacol.* 378(3): 323-30 (1999).

McFadyen et al., Modifications of the cyclic μ receptor selective tetrapeptide Tyr-C not D-Cys-Phe-D-Pen ¾ NH2 (ET): Effects on opioid receptor binding and activation. *J. Peptide Res.* 55(3): 255-61 (2000).

McFadyen et al., Tetrapeptide derivatives of [D-Pen(2),D-Pen(5)]-enkephalin (DPDPE) lacking an N-terminal tyrosine residue are agonists at the mu-opioid receptor. *J. Pharmacol. Exp. Ther.* 295(3): 960-6 (2000).

Merrifield, Solid Phase Peptide Synthesis. I. The Synthesis of a Tetrapeptide. *J. Am. Chem. Soc.* 85: 2149-54 (1963).

Morris et al., Cell-penetrating peptides: from molecular mechanisms to therapeutics. *Biol. Cell.* 100: 201-17 (2008).

Mosberg et al., Development of model for the δ opioid receptor pharmacophore. 2. Conformationally restricted Phe3 replacements in the cyclic δ receptor selective tetrapeptide Tyr-c[D-Cys-Phe-D-Pen]OH (JOM-13), *J. Med. Chem.* 37 (25): 4384-91 (1994).

Nielsen et al., A novel delta opioid receptor antagonist, SoRI-9409, produces a selective and long-lasting decrease in ethanol consumption in heavy-drinking rats. *Biol. Psychiatry*, 64(11): 974-81 (2008).

O'Donnell et al., Solid-phase unnatural peptide synthesis (UPS). *J. Am. Chem. Soc.* 118: 6070-1 (1996).

Przydzial et al., Roles of residues 3 and 4 in cyclic tetrapeptide ligand recognition by the kappa-opioid receptor. *J. Pept. Res.* 65(3): 333-42 (2005).

Purington et al., Development and in vitro characterization of a novel bifunctional μ-agonist δ-antagonist opioid tetrapeptide. *ACS Chem. Biol.*, 6(12): 1375-81 (2011).

Purington et al., Pentapeptides displaying mu opioid receptor agonist and delta opioid receptor partial agonist/antagonist properties. *J. Med. Chem.* 52(23): 7724-31 (2009).

Salvadori et al., Further studies on the Dmt-Tic pharmacophore: hydrophobic substituents at the C-terminus endow delta antagonists to manifest mu agonism or mu antagonism. *J. Med. Chem.* 42: 5010-9 (1999).

Sasaki et al., Endomorphin 2 analogues containing Dmp residue as an aromatic amino acid surrogate with high mu-opioid receptor affinity and selectivity. *Bioorg. Med. Chem.* 11: 675-8 (2003).

Schiller et al., The opioid mu agonist/delta antagonist DIPP-NH(2)[Psi] produces a potent analgesic effect, no physical dependence, and less tolerance than morphine in rats. *J. Med. Chem.* 42(18): 3520-6 (1999).

Sebbage, Cell-penetrating peptides and their therapeutic applications. *Bioscience Horizons*, 2(1): 64-72 (2009).

Smith et al., Solid-phase peptide synthesis and biological activity of bovine thymopoietin II (bTP-II). *Int. J. Peptide Protein Res.* 44: 183 (1994).

Traynor et al., Modulation by mu-opioid agonists of guanosine-5'-O-(3[35S]thio)triphosphate binding to membranes from human neuroblastoma SH-SY5Y cells. *Mol. Pharmacol.* 47(4): 848-54 (1995).

Woolfe et al., The evaluation of the analgesic action of pethidine hydrochloride (Demerol). *J. Pharmacol. Exp. Ther.* 1944; 80:300-307).

International Search Report and Written Opinion of the International Searching Authority issued in connection with International Application No. PCT/US2012/043819, dated Sep. 4, 2012.

FIGURE 2

| Compound | Sequence | Ki, nM (MOR) | Ki, nM (DOR) | Ki, nM (KOR) |
|---|---|---|---|---|
| JOM-6 | Tyr-c(S-CH$_2$-CH$_2$-S)-[D-Cys-Phe-D-Pen]NH$_2$ | 0.3 ± 0.04 | 25 ± 1.5 | n.d. |
| 1 | Dmt-c(S-CH$_2$-CH$_2$-S)-[D-Cys-Aci-D-Pen]NH$_2$ | 0.6 ± 0.1 | 0.9 ± 0.2 | 9.8 ± 3.6 |
| 2 | Dmt-c(S-CH$_2$-CH$_2$-S)-[D-Cys-Aci-D-Pen]OH | 2.4 ± 0.7 | 2.3 ± 0.5 | 776 ± 149 |
| DIPP(Ψ)NH$_2$ | Dmt-Tic(Ψ)[CH$_2$NH$_2$]Phe-Phe-NH$_2$ | 0.4 ± 0.1 | 0.4 ± 0.04 | 3.9 ± 0.2 |
|  | Dmt-Tic-Gly-NH-Bzl | 26 ± 8 | 0.2 ± 0.06 | 128 ± 42 |

FIGURE 3

| Compound | Sequence | MOR EC$_{50}$, nM | MOR % max. | DOR EC$_{50}$ | DOR % max. | KOR EC$_{50}$ | KOR % max. |
|---|---|---|---|---|---|---|---|
| 1 | Dmt-c(S-CH$_2$-CH$_2$-S)-[D-Cys-Aci-D-Pen]NH$_2$ | 0.4 ± 0.02 | 58 ± 8 | 1.4 ± 0.4 | 37 ± 4 | 0.4 ± 0.3 | 3 ± 3 |
| 2 | Dmt-c(S-CH$_2$-CH$_2$-S)-[D-Cys-Aci-D-Pen]OH | 4.7 ± 0.7 | 59 ± 11 | n.d. | 0 | n.d. | 0 |
| DIPP(Ψ)NH$_2$ | Dmt-Tic(Ψ)[CH$_2$NH$_2$]Phe-Phe-NH$_2$ | 5.7 ± 3.3 | 18 ± 1 | n.d. | 2 ± 2 | 125 ± 42 | 11 ± 3 |
|  | Dmt-Tic-Gly-NH-Bzl | 1.4 ± 0.2 | 7 ± 2 | n.d. | 21 ± 4 | n.d. | 5 ± 1 |
| Morphine |  | 194 ± 21 | 57 ± 5 | n.d. | n.d. | n.d. | n.d. |
| endomorphin-2 |  | 125 ± 31 | 49 ± 7 | n.d. | n.d. | n.d. | n.d. |

FIGURE 4

| Compound | Sequence | Ki, nM | | |
|---|---|---|---|---|
| | | (MOR) | (DOR) | (KOR) |
| VRP-13 | Dmt-c(S-CH$_2$-CH$_2$-S)-[D-Cys-Aci-D-Pen]Ser-OH | 10.3 ± 2.3 | 4.5 ± 1.0 | 7100 ± 1260 |
| VRP-15 | Dmt-c(S-CH$_2$-CH$_2$-S)-[D-Cys-Aci-D-Pen]Thr-OH | 18.0 ± 3.9 | 6.3 ± 1.2 | 32700 ± 9800 |
| VRP-19 | Dmt-c(S-CH$_2$-CH$_2$-S)-[D-Cys-Aci-D-Pen]Ser-NH$_2$ | 1.7 ± 0.8 | 2.7 ± 0.8 | 174 ± 13.7 |
| VRP-21 | Dmt-c(S-CH$_2$-CH$_2$-S)-[D-Cys-Aci-D-Pen]Thr-NH$_2$ | 1.9 ± 0.3 | 2.7 ± 0.3 | 607 ± 56 |
| VRP-24 | Dmt-c(S-CH$_2$-CH$_2$-S)-[D-Cys-Aci-D-Pen]Arg-NH$_2$ | 0.43 ± 0.06 | 3.6 ± 0.3 | 65.3 ± 5.8 |
| VRP-26 | Dmt-c(S-CH$_2$-CH$_2$-S)-[D-Cys-Aci-D-Pen](Glc)Ser-NH$_2$ | 4.7 ± 0.3 | 4.7 ± 0.1 | 810 ± 155 |

FIGURE 5

| Compound | Sequence | MOR | | DOR | |
|---|---|---|---|---|---|
| | | EC$_{50}$, nM | % max. | EC$_{50}$ | % max. |
| VRP-19 | Dmt-c(S-CH$_2$-CH$_2$-S)-[D-Cys-Aci-D-Pen]Ser-NH$_2$ | 6.64 ± 4.8 | 44 ± 11 | 22.4 ± 12.7 | 7.53 ± 1.2 |
| VRP-24 | Dmt-c(S-CH$_2$-CH$_2$-S)-[D-Cys-Aci-D-Pen]Arg-NH$_2$ | 19.6 ± 6.0 | 37.1 ± 11 | 210 ± 150 | 9.3 ± 6.2 |
| VRP-26 | Dmt-c(S-CH$_2$-CH$_2$-S)-[D-Cys-Aci-D-Pen](Glc)Ser-NH$_2$ | 15.3 ± 4.5 | 54.4 ± 6.8 | n.s. | n.s. |

COMPOUND AND METHOD FOR MODULATING OPIOID RECEPTOR ACTIVITY

CROSS-REFERENCE TO RELATED APPLICATIONS

This application claims the benefit of priority of U.S. Provisional Patent Application No. 61/500,363, filed Jun. 23, 2011. The disclosure of the priority application is incorporated herein by reference.

GRANT FUNDING DISCLOSURE

This invention was made with government support under grant number R01 DA003910, awarded by the National Institutes of Health. The government has certain rights in the invention.

FIELD OF DISCLOSURE

The invention relates to compounds and methods of modulating mu-opioid receptor and/or delta-opioid receptor activity.

BACKGROUND OF THE INVENTION

Opioid receptors are G protein-coupled receptors found in the brain, spinal cord, and digestive tract that have a wide variety of biological function, including controlling pain sensation. There are three recognized "classical" opioid receptor subtypes: mu-opioid receptors (MOR), delta-opioid receptors (DOR), and kappa-opioid receptors (KOR). The natural ligands for opioid receptors include enkephalins, endorphins, endomorphins, and dynorphins, and an abundance of non-peptide or synthetic ligands have been discovered or developed to modulate opioid receptor activity. Opioid drugs, including morphine, are the primary treatment for, e.g., post-operative and chronic pain conditions. Side-effects of opioid administration (e.g., tolerance, drug dependence/addiction, respiration depression, constipation, nausea, pruritus, sedation, and mood swings), however, limit opioids' therapeutic potential.

Despite a considerable amount of research into opioid-based therapeutics, there remains a need for opioid receptor modulators that provide analgesia while minimizing the adverse effects associated with opioid use.

SUMMARY OF THE INVENTION

The invention provides a compound having a structure of formula (I):

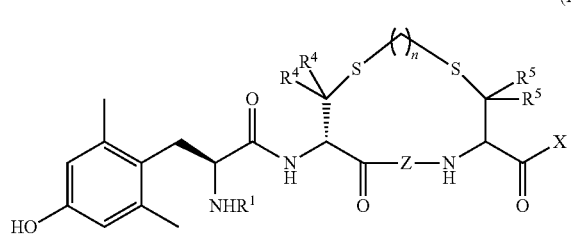

(I)

wherein, $R^1$ is H, C(NH)$NH_2$, an amino acid, or a peptide; X is OH, $NH_2$, $NHR^2$, $NR^2R^3$, an amino acid, or a peptide; $R^2$ and $R^3$ are the same or different and selected from alkyl, alkylenearyl, or alkyleneheteroaryl; each $R^4$ and $R^5$ is independently H or $CH_3$; Z is an amino acid selected from the group consisting of 2-amino-2,3-dihydro-1H-indene-2-carboxylic acid (Aci); 2-amino-1,2,3,4-tetrahydronaphthalene-2-carboxylic acid (Atc); 6-amino-6,7,8,9-tetrahydro-5H-benzo[7]annulene 6-carboxylic acid; cyclohexylalanine (Cha); cyclohexylglycine (Chg); homophenylalanine (Hfe); 1-naphtylalanine (1-Nal); 2-napthylalanine (2-Nal); 1,2,3,4-tetrahydroisoquinoline-3-carboxylic acid (Tic); and octahydro-1H-indole-2-carboxylic acid (Oic); n is 0, 1, 2, 3, or 4; with the proviso that X is not $NH_2$ when $R^1$ is H, each $R^4$ is H, each $R^5$ is $CH_3$, Z is Aci, and n is 2. The invention also includes a pharmaceutically acceptable salt, ester or solvate of formula (I). In various embodiments, the compound is a mu-opioid receptor (MOR) agonist and a delta-opioid receptor (DOR) antagonist and/or displays substantially equivalent binding affinity for MOR and DOR.

Additionally, the invention includes a composition comprising the compound and a pharmaceutically acceptable carrier, as well as a method of modulating opioid receptor activity, a method of treating pain in a subject, a method for treating a mu-opioid receptor (MOR) mediated disorder in a subject, a method for treating a delta-opioid receptor (DOR) mediated disorder in a subject, and a method for treating a mu-opioid receptor (MOR) mediated disorder and a delta-opioid receptor (DOR) mediated disorder in a subject.

The following numbered paragraphs each succinctly define one or more exemplary variations of the invention:

1. A compound having a structure of formula (I):

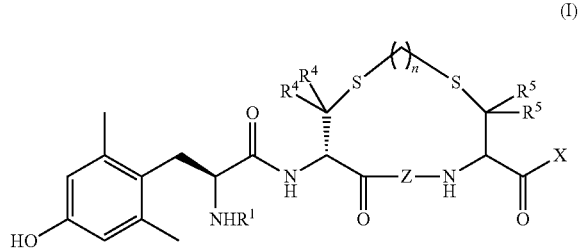

(I)

wherein
$R^1$ is H, C(NH)$NH_2$, an amino acid, or a peptide;
X is OH, $NH_2$, $NHR^2$, $NR^2R^3$, an amino acid, or a peptide;
$R^2$ and $R^3$ are the same or different and selected from alkyl, alkylenearyl, or alkyleneheteroaryl;
each $R^4$ and $R^5$ is independently H or $CH_3$;
Z is an amino acid selected from the group consisting of 2-amino-2,3-dihydro-1H-indene-2-carboxylic acid (Aci); 2-amino-1,2,3,4-tetrahydronaphthalene-2-carboxylic acid (Atc); 6-amino-6,7,8,9-tetrahydro-5H-benzo[7]annulene 6-carboxylic acid; cyclohexylalanine (Cha); cyclohexylglycine (Chg); homophenylalanine (Hfe); 1-naphthylalanine (1-Nal); 2-naphthylalanine (2-Nal); 1,2,3,4-tetrahydroisoquinoline-3-carboxylic acid (Tic); and octahydro-1H-indole-2-carboxylic acid (Oic);
n is 0, 1, 2, 3, or 4;
with the proviso that X is not $NH_2$ when $R^1$ is H, each $R^4$ is H, each $R^5$ is $CH_3$, Z is Aci, and n is 2;
or a pharmaceutically acceptable salt, ester or solvate thereof.

2. The compound of paragraph 1, wherein $R^1$ is arginine.

3. The compound of paragraph 1 or paragraph 2, wherein X is an amino acid selected from the group consisting of serine, threonine, arginine, homoarginine, and modified residues thereof.

4. The compound of any one of paragraphs 1-3, wherein X is serine or threonine.

5. The compound of any one of paragraphs 1-3, wherein X is a modified residue selected from the group consisting of serine, threonine, arginine, and homoarginine, and wherein the modified residue is substituted with one or more of $NH_2$, OH, alkyl substituents, alkylenearyl substituents, alkyloxy substituents, and/or alkylenearyloxy substituents.

6. The compound of paragraph 5, wherein X is a modified arginine or homoarginine residue having the structure:

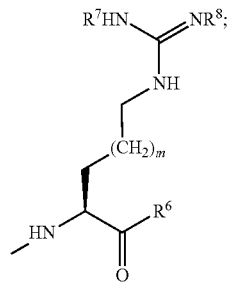

wherein m is 1 or 2;

$R^6$ is selected from the group consisting of $NH_2$, OH, and $OR^9$; and $R^7$, $R^8$, and $R^9$ are individually selected from the group consisting of alkyl substituents and alkylenearyl substituents.

7. The compound of any one of paragraphs 1-6, wherein $R^1$ and/or X is a glycosylated amino acid or a glycosylated peptide.

8. The compound of any one of paragraphs 1-7, wherein X is a glycosylated amino acid or glycosylated peptide comprising a glycosyl group selected from the group consisting of alpha and beta anomers of cellobiose, D-glucose, fucose, lactose, maltose, maltotriose, melibiose, and xylose.

9. The compound of any one of paragraphs 1-8, wherein $R^1$ and/or X is a cell penetrating peptide.

10. The compound of any one of paragraphs 1-9, wherein each $R^4$ is H.

11. The compound of any one of paragraphs 1-9, wherein one $R^4$ is H and one $R^4$ is $CH_3$.

12. The compound of any one of paragraphs 1-9, wherein each $R^4$ is $CH_3$.

13. The compound of any one of paragraphs 1-12, wherein each $R^5$ is H.

14. The compound of any one of paragraphs 1-12, wherein one $R^5$ is H and one $R^4$ is $CH_3$.

15. The compound of any one of paragraphs 1-12, wherein one $R^5$ is H and one $R^5$ is $CH_3$.

16. The compound of any one of paragraphs 1-12, wherein each $R^5$ is $CH_3$.

17. The compound of any one of paragraphs 1-16, wherein n is 0.

18. The compound of any one of paragraphs 1-16, wherein n is 1.

19. The compound of any one of paragraphs 1-16, wherein n is 2.

20. The compound of any one of paragraphs 1-16, wherein n is 3.

21. The compound of any one of paragraphs 1-16, wherein n is 4.

22. The compound of any one of paragraphs 1-21, wherein Z is Aci.

23. The compound of any one of paragraphs 1-21, wherein Z is Atc.

24. The compound of any one of paragraphs 1-21, wherein Z is 6-amino-6,7,8,9-tetrahydro-5H-benzo[7]annulene 6-carboxylic acid.

25. The compound of any one of paragraphs 1-21, wherein Z is Cha.

26. The compound of any one of paragraphs 1-21, wherein Z is Chg.

27. The compound of any one of paragraphs 1-21, wherein Z is Hfe.

28. The compound of any one of paragraphs 1-21, wherein Z is 1-Nal.

29. The compound of any one of paragraphs 1-21, wherein Z is 2-Nal.

30. The compound of any one of paragraphs 1-21, wherein Z is Tic.

31. The compound of any one of paragraphs 1-21, wherein Z is Oic.

32. The compound of any one of paragraphs 1-16 having a structure:

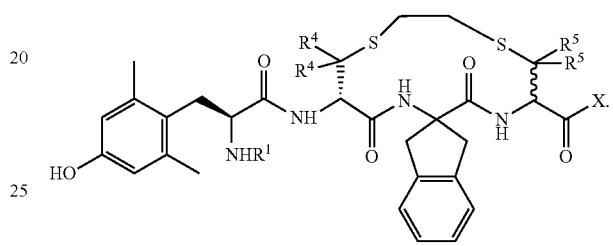

33. The compound of any one of paragraphs 1-16 having a structure:

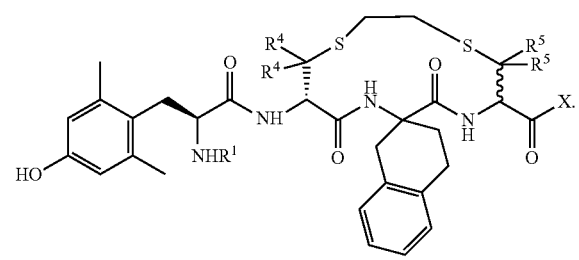

34. The compound of any one of paragraphs 1-16 having a structure:

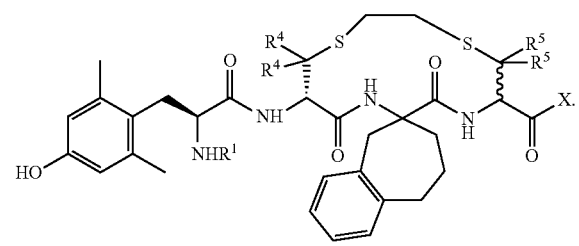

35. The compound of any one of paragraphs 1-16 having a structure:

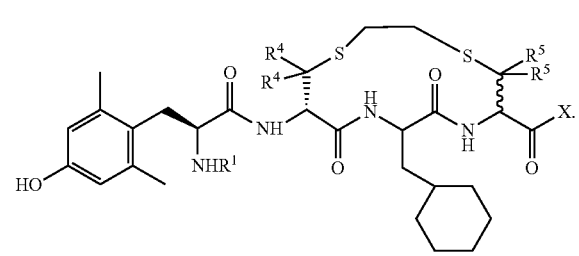

36. The compound of any one of paragraphs 1-16 having a structure:

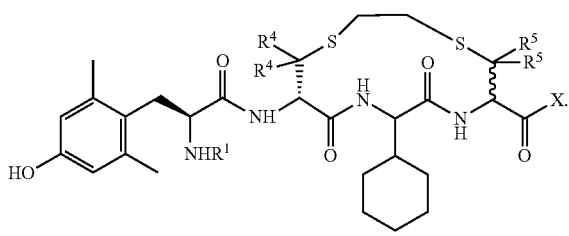

37. The compound of any one of paragraphs 1-16 having a structure:

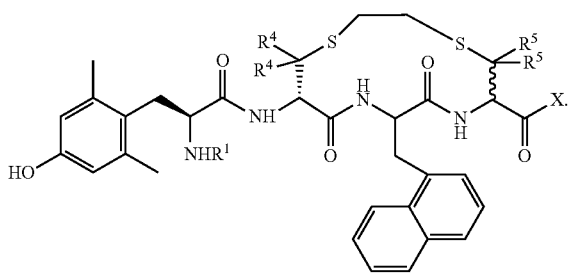

38. The compound of any one of paragraphs 1-16 having a structure:

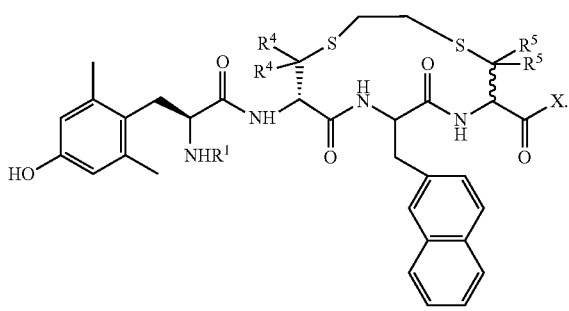

39. The compound of any one of paragraphs 1-16 having a structure:

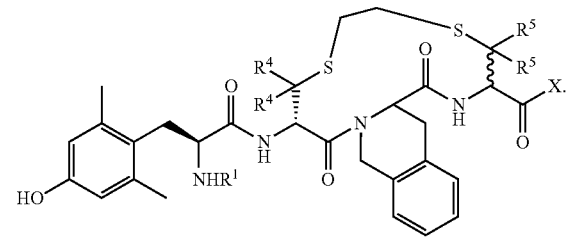

40. The compound of any one of paragraphs 1-16 having a structure:

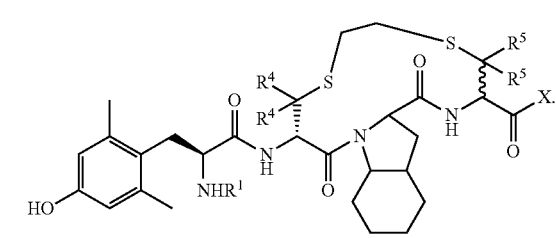

41. The compound of paragraph 1 having a structure:

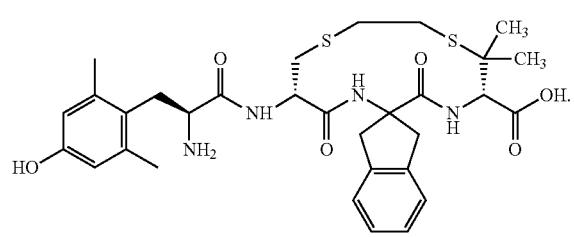 [SMILES: Cc1cc(O)cc(C)c1C[C@H](N)C(=O)N[C@@H]1CSCCSC(C)(C)[C@H](C(=O)O)NC(=O)C2(Cc3ccccc3C2)NC1=O]

42. The compound of paragraph 1 having a structure:

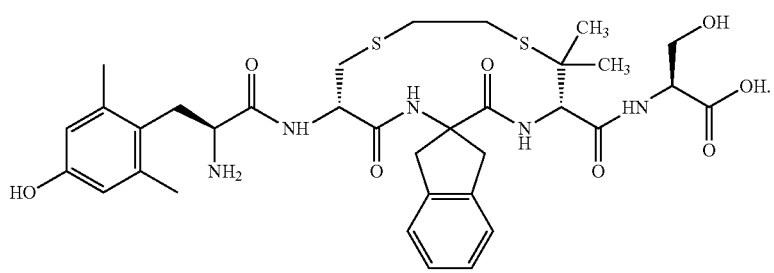 [SMILES: Cc1cc(O)cc(C)c1C[C@H](N)C(=O)N[C@@H]1CSCCSC(C)(C)[C@H](C(=O)N[C@@H](CO)C(=O)O)NC(=O)C2(Cc3ccccc3C2)NC1=O]

43. The compound of paragraph 1 having a structure:

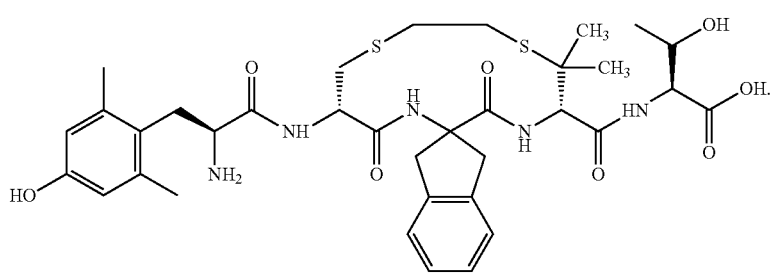 [SMILES: Cc1cc(O)cc(C)c1C[C@H](N)C(=O)N[C@@H]1CSCCSC(C)(C)[C@H](C(=O)N[C@H](C(=O)O)C(C)O)NC(=O)C2(Cc3ccccc3C2)NC1=O]

44. The compound of paragraph 1 having a structure:

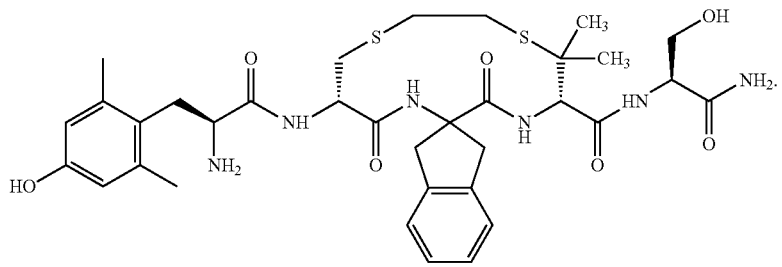 [SMILES: Cc1cc(O)cc(C)c1C[C@H](N)C(=O)N[C@@H]1CSCCSC(C)(C)[C@H](C(=O)N[C@@H](CO)C(N)=O)NC(=O)C2(Cc3ccccc3C2)NC1=O]

45. The compound of paragraph 1 having a structure:

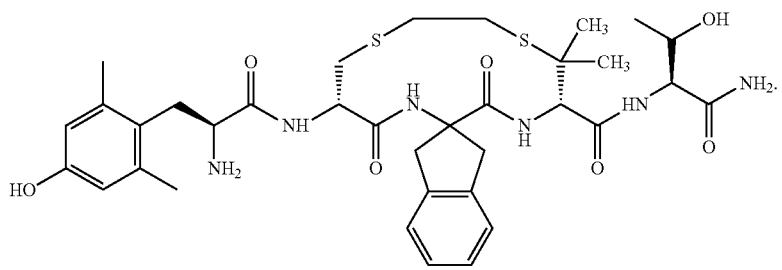 [SMILES: Cc1cc(O)cc(C)c1C[C@H](N)C(=O)N[C@@H]1CSCCSC(C)(C)[C@H](C(=O)N[C@H](C(N)=O)C(C)O)NC(=O)C2(Cc3ccccc3C2)NC1=O]

46. The compound of paragraph 1 having a structure:

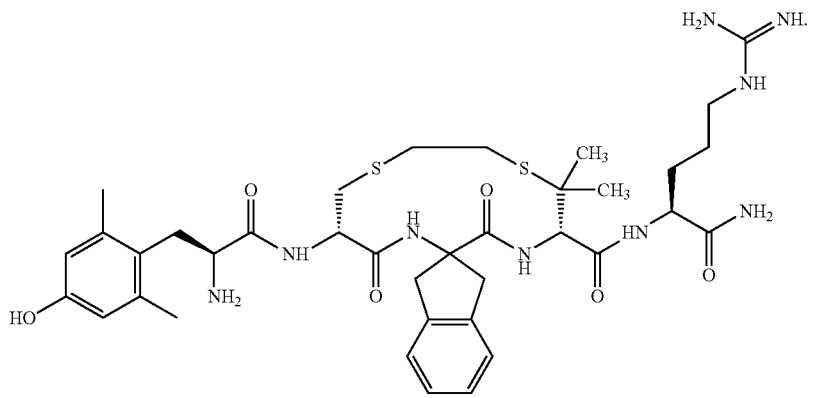 [SMILES: Cc1cc(O)cc(C)c1C[C@H](N)C(=O)N[C@@H]1CSCCSC(C)(C)[C@H](C(=O)N[C@@H](CCCNC(=N)N)C(N)=O)NC(=O)C2(Cc3ccccc3C2)NC1=O]

47. The compound of paragraph 1 having a structure:

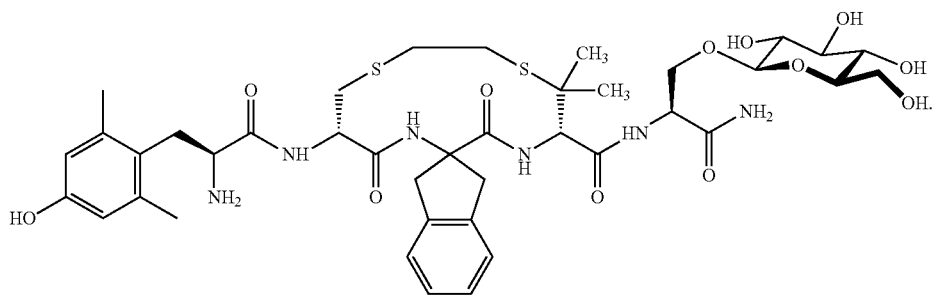

48. The compound of any one of paragraphs 1-47 conjugated to an entity that enhances the half life of the compound, enhances cellular uptake of the compound, and/or enhances transport across the blood-brain barrier.

49. The compound of paragraph 48, wherein the compound is conjugated to a water soluble polymer.

50. The compound of paragraph 48, wherein the compound is conjugated to albumin, an antibody or fragment thereof, or a proline-alanine-serine multimer (PASylation).

51. The compound of any one of paragraphs 1-50, wherein the compound is a mu-opioid receptor (MOR) agonist and a delta-opioid receptor (DOR) antagonist.

52. The compound of any one of paragraphs 1-51, wherein the compound displays substantially equivalent binding affinity for MOR and DOR.

53. The compound of any one of paragraphs 1-52, wherein the compound binds MOR and DOR with an affinity at least 100 times greater than the compound binds kappa-opioid receptor (KOR).

54. A method of modulating the activity of MOR and/or DOR, the method comprising exposing a MOR and/or a DOR to the compound of any one of paragraphs 1-53.

55. A composition comprising the compound of any one of paragraphs 1-53 and a pharmaceutically acceptable carrier.

56. The composition of paragraph 55 further comprising one or more therapeutic agents.

57. A method of treating pain in a subject, the method comprising administering to the subject the composition of paragraph 55 or paragraph 56 in an amount sufficient to induce analgesia.

58. The method of paragraph 57, wherein administration of the composition of paragraph 55 or paragraph 56 attenuates physical dependence or tolerance associated with opioid use.

59. A method for treating a mu-opioid receptor (MOR) mediated disorder in a subject, the method comprising administering to the subject the composition of paragraph 55 or paragraph 56 in an amount sufficient to ameliorate the disorder.

60. A method for treating a delta-opioid receptor (DOR) mediated disorder in a subject, the method comprising administering to the subject the composition of paragraph 55 or paragraph 56 in an amount sufficient to ameliorate the disorder.

61. A method for treating a mu-opioid receptor (MOR) mediated disorder and a delta-opioid receptor (DOR) mediated disorder in a subject, the method comprising administering to the subject the composition of paragraph 55 or paragraph 56 in an amount sufficient to ameliorate the disorder.

62. The method of any one of paragraphs 57-61, wherein the composition is administered intrathecally, intravenously, subcutaneously, intramuscularly, or orally.

63. The method of any one of paragraphs 57-62, further comprising administering to the subject an additional therapeutic agent and/or an agent that facilitates transport across the blood-brain barrier.

The foregoing summary is not intended to define every aspect of the invention, and additional aspects are described in other sections, such as the Detailed Description. The entire document is intended to be related as a unified disclosure, and it should be understood that all combinations of features described herein are contemplated, even if the combination of features are not found together in the same sentence, or paragraph, or section of this document. In addition, the invention includes, as an additional aspect, all embodiments of the invention narrower in scope in any way than the variations specifically mentioned above. With respect to aspects of the invention described or claimed with "a" or "an," it should be understood that these terms mean "one or more" unless context unambiguously requires a more restricted meaning. With respect to elements described as one or more within a set, it should be understood that all combinations within the set are contemplated. If aspects of the invention are described as "comprising" a feature, embodiments also are contemplated "consisting of" or "consisting essentially of" the feature.

Although the applicant(s) invented the full scope of the claims appended hereto, the claims appended hereto are not intended to encompass within their scope the prior art work of others. Therefore, in the event that statutory prior art within the scope of a claim is brought to the attention of the applicants by a Patent Office or other entity or individual, the applicant(s) reserve the right to exercise amendment rights under applicable patent laws to redefine the subject matter of such a claim to specifically exclude such statutory prior art or obvious variations of statutory prior art from the scope of such a claim. Variations of the invention defined by such amended claims also are intended as aspects of the invention. Additional features and variations of the invention will be apparent to those skilled in the art from the entirety of this application, and all such features are intended as aspects of the invention.

BRIEF DESCRIPTION OF THE FIGURES

FIG. 2 is a table comparing the binding affinities (Ki (nM)) of compound 1, compound 2, JOM-6, DIPP(Ψ)NH$_2$, and Dmt-Tic-Gly-NH-Bzl for mu-opioid receptor (MOR), delta-opioid receptor (DOR), and kappa-opioid receptor (KOR) in cell membrane preparations. Experiments were performed as described in the Example, and affinity was determined by non-linear regression following displacement of 0.2 nM [$^3$H] diprenorphine from membrane preparations of opioid receptors expressed in C6-rat glioma (MOR and DOR) or Chinese hamster ovary cells (KOR). The JOM-6 data was taken from McFadyen et al., *J. Pharmacol. Exp. Ther.* 2000; 295(3): 960-966.

FIG. 3 is a table comparing the efficacies (EC50 (nM) and % max) of compound 1, compound 2, DIPP(Ψ)NH$_2$, Dmt-Tic-Gly-NH-Bzl, morphine, and endomorphin-2 for stimulation of MOR, DOR, and KOR in cell membrane preparations. EC50 values were determined from non-linear regression analysis of [$^{35}$S]GTPγS incorporation as described in the Example. Percent maximum (% max) values represent the percent of maximal G protein stimulation obtained with 10 μM compound compared to a 10 μM concentration of standard agonists DAMGO (MOR), DPDPE (DOR), and U69, 593 (KOR). "n.d." denotes "data was not determined."

FIG. 4 is a table comparing the binding affinities (Ki (nM)) of VRP-13, VRP-15, VRP-19, VRP-21, VRP-24, and VRP-26 for mu-opioid receptor (MOR), delta-opioid receptor (DOR), and kappa-opioid receptor (KOR) in cell membrane preparations. Experiments were performed as described in the Example, and affinity was determined by non-linear regression following displacement of 0.2 nM [$^3$H]diprenorphine from membrane preparations of opioid receptors expressed in C6-rat glioma (MOR and DOR) or Chinese hamster ovary cells (KOR).

FIG. 5 is a table comparing the efficacies (EC50(nM) and % max) of VRP-19, VRP-24, and VRP-26 for stimulation of MOR and DOR, in cell membrane preparations. EC50 values were determined from non-linear regression analysis of [$^{35}$S] GTPγS incorporation as described in the Example. Percent maximum (% max) values represent the percent of maximal G protein stimulation obtained with 10 μM compound compared to a 10 μM concentration of standard agonists DAMGO (MOR), and DPDPE (DOR). "n.s." denotes "does not stimulate," i.e., the compound acts as an antagonist for the receptor.

DETAILED DESCRIPTION OF THE INVENTION

Figure 1:
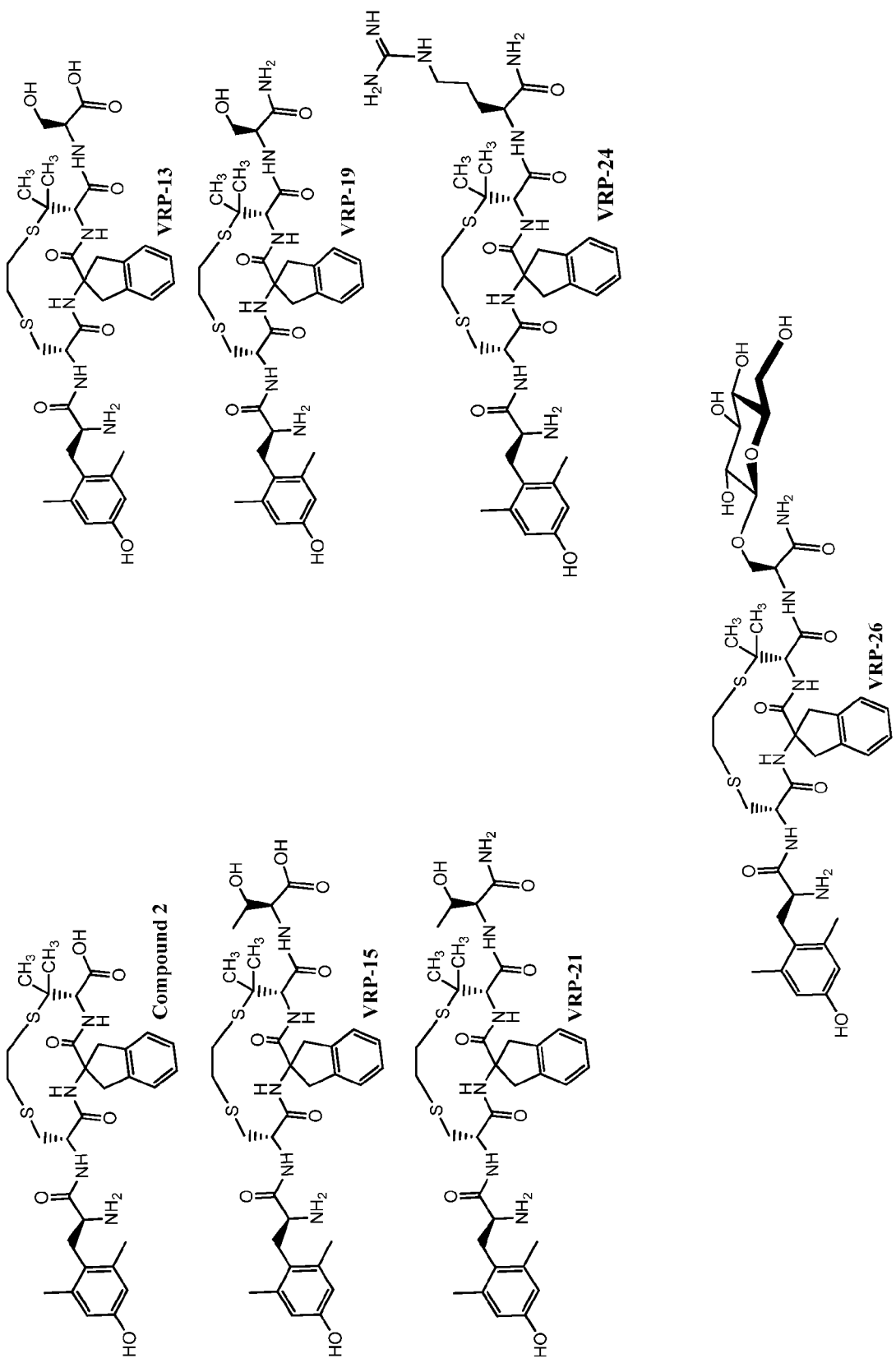
FIG. 1 depicts chemical structures of compounds assayed for opioid receptor binding affinity, agonist/antagonist properties, and analgesic effects.

The invention provides bifunctional compounds having two opioid receptor actions: MOR agonism to, e.g., promote analgesia, and DOR antagonism to, e.g., minimize or prevent undesired effects associated with opioid use, including tolerance or dependence. The bifunctional compounds are superior to combination therapies comprising two drugs acting separately at each individual receptor, the therapeutic effect of which could be hampered by increased potential 'off-target' effects, differences in pharmacokinetic profiles, and user compliance.

The invention includes a compound having a structure of formula (I):

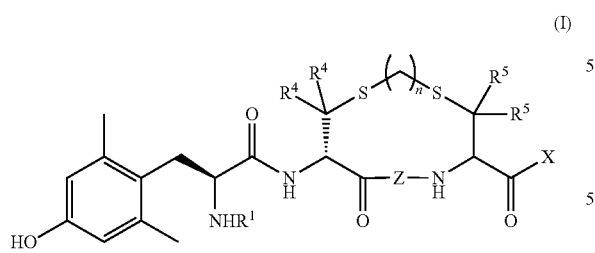

(I)

In formula (I), R$^1$ is H, C(NH)NH$_2$, an amino acid, or a peptide; X is OH, NH$_2$, NHR$^2$, NR$^2$R$^3$, an amino acid, or a peptide; R$^2$ and R$^3$ are the same or different and selected from alkyl, alkylenearyl, or alkyleneheteroaryl; each R$^4$ and R$^5$ is independently H or CH$_3$; Z is an amino acid selected from the group consisting of 2-amino-2,3-dihydro-1H-indene-2-carboxylic acid (Aci); 2-amino-1,2,3,4-tetrahydronaphthalene-2-carboxylic acid (Atc); 6-amino-6,7,8,9-tetrahydro-5H-benzo[7]annulene 6-carboxylic acid; cyclohexylalanine (Cha); cyclohexylglycine (Chg); homophenylalanine (Hfe); 1-naphthylalanine (1-Nal); 2-naphthylalanine (2-Nal); 1,2,3,4-tetrahydroisoquinoline-3-carboxylic acid (Tic); and octahydro-1H-indole-2-carboxylic acid (Oic); n is 0, 1, 2, 3, or 4; with the proviso that X is not NH$_2$ when R$^1$ is H, each R$^4$ is H, each R$^5$ is CH$_3$, Z is Aci, and n is 2; or a pharmaceutically acceptable salt, ester or solvate thereof.

All combinations of substituents of formula (I) (except the combination of X=NH$_2$, R$^1$=H, R$^4$=H, R$^5$=CH$_3$, Z=Aci, and n=2) is contemplated herein. For example, the invention includes compounds having the following structures:

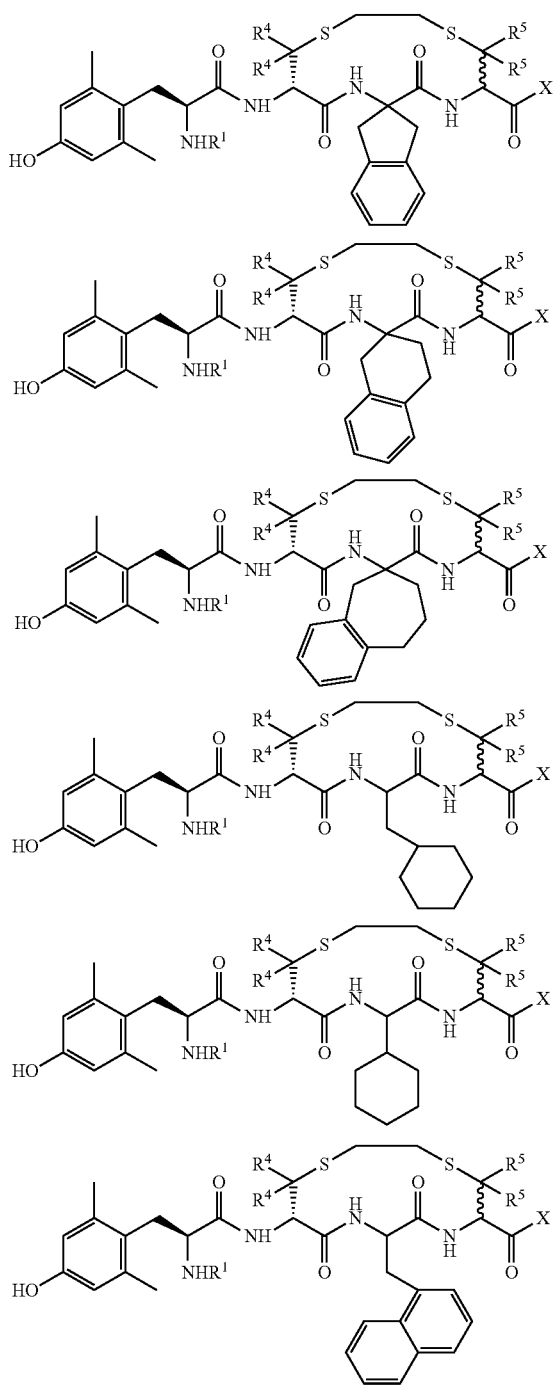

-continued

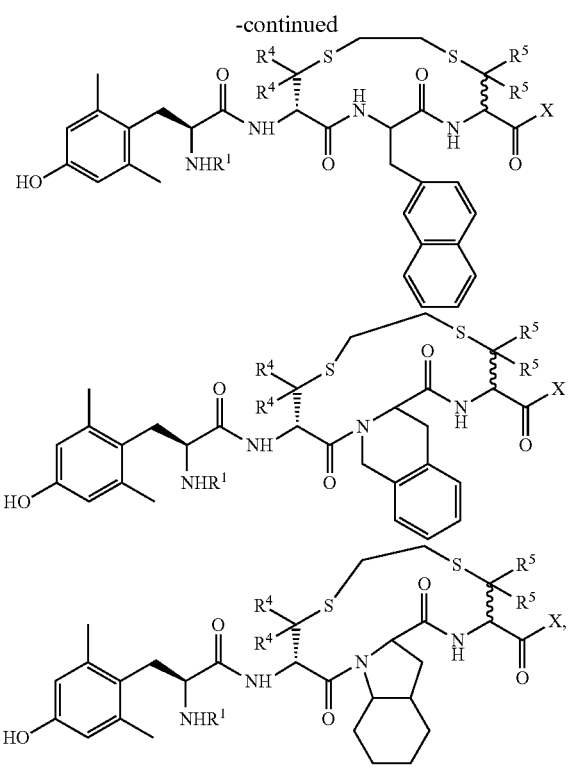

wherein $R^1$, X, $R^4$, and $R^5$ are defined above. In one aspect, the compound comprises the structure:

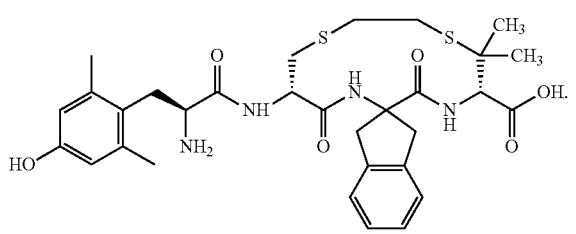

The term "alkyl" used herein refers to a saturated or unsaturated straight or branched chain hydrocarbon group of one to ten carbon atoms, including, but not limited to, methyl, ethyl, n-propyl, isopropyl, n-butyl, isobutyl, tert-butyl, n-hexyl, and the like. Specifically contemplated is a $C_1$-$C_6$ alkyl, i.e., an alkyl group having one to six carbons.

The term "alkylene" used herein refers to an alkyl group having a substituent. For example, the term "alkylenearyl" refers to an alkyl group substituted with an aryl group. For example, an alkylene group can be —$CH_2CH_2$— or —$CH_2$—. The terms "alkyloxy" and "alkylenearyloxy" refer to an alkyl group or alkylenearyl group substituted with an oxygen, respectively.

As used herein, the term "aryl" refers to a monocyclic or polycyclic aromatic group, preferably a monocyclic or bicyclic aromatic group, e.g., phenyl or naphthyl. Unless otherwise indicated, an aryl group can be unsubstituted or substituted with one or more, and in particular one to four groups independently selected from, for example, halo, alkyl, alkenyl, $OCF_3$, $NO_2$, CN, NC, OH, alkoxy, amino, $CO_2H$, $CO_2$alkyl, aryl, and heteroaryl. Exemplary aryl groups include, but are not limited to, phenyl, naphthyl, tetrahydronaphthyl, chlorophenyl, methylphenyl, methoxyphenyl, trifluoromethylphenyl, nitrophenyl, 2,4-methoxychlorophenyl, and the like.

As used herein, the term "heteroaryl" refers to a monocyclic or bicyclic ring system containing one or two aromatic rings and containing at least one nitrogen, oxygen, or sulfur atom in an aromatic ring. Unless otherwise indicated, a heteroaryl group can be unsubstituted or substituted with one or more, and in particular one to four, substituents selected from, for example, halo, alkyl, alkenyl, $OCF_3$, $NO_2$, CN, NC, OH, alkoxy, amino, $CO_2H$, $CO_2$alkyl, aryl, and heteroaryl. In some cases, the heteroaryl group is substituted with one or more of alkyl and alkoxy groups. Examples of heteroaryl groups include, but are not limited to, thienyl, furyl, pyridyl, oxazolyl, quinolyl, thiophenyl, isoquinolyl, indolyl, triazinyl, triazolyl, isothiazolyl, isoxazolyl, imidazolyl, benzothiazolyl, pyrazinyl, pyrimidinyl, thiazolyl, and thiadiazolyl.

In various embodiments of the invention, $R^1$ and/or X is an amino acid or a peptide, optionally a glycosylated amino acid or a glycosylated peptide. "Amino acid" encompasses the 20 conventional amino acids as well as non-conventional and modified amino acids known in the art, all of which may exist as D- or L-isomers. See, e.g., International Patent Publication No. 2010/071894, the disclosure of which, including the disclosure of non-conventional amino acids (see, e.g., Tables 1 and 2), is hereby incorporated by reference. For example, X can be serine, threonine, arginine, or homoarginine. In one aspect, X can be serine, threonine, arginine, or homoarginine, substituted with one or more of $NH_2$, OH, alkyl substituents, alkylenearyl substituents, alkyloxy substituents, and/or alkylenearyloxy substituents. For example, X can be a modified arginine or homoarginine residue having the structure:

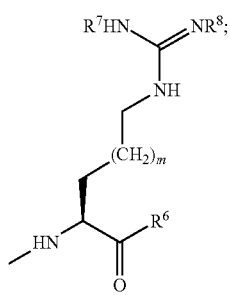

wherein m is 1 or 2, $R^6$ is selected from the group consisting of $NH_2$, OH, and $OR^9$; and $R^7$, $R^8$, and $R^9$ are individually selected from the group consisting of alkyl substituents and alkylenearyl substituents. The invention includes compounds of formula (I) wherein $R^1$ is arginine and/or X is serine or threonine. By "peptide" is meant a polymer of at least two amino acids and typically no more than 50 amino acids. The peptide at $R^1$ and/or X, in some instances, exhibits a desired biological activity or function; enhances transport of the compound across the blood-brain barrier; and/or facilitates synthesis, handling, purification, or use of the compound. Examples of peptides that facilitate synthesis, handling, or purification of the peptide include, but are not limited to a His tag, a FLAG tag, a strep tag, a myc tag, and a marker protein. A "glycosylated amino acid" or "glycosylated peptide" is conjugated (chemically linked) with a glycosyl group. Examples of glycosyl groups include, but are not limited to, alpha and beta anomers of cellobiose, D-glucose, fucose, lactose, maltose, maltotriose, melibiose, and xylose.

Examples of compounds described herein include:
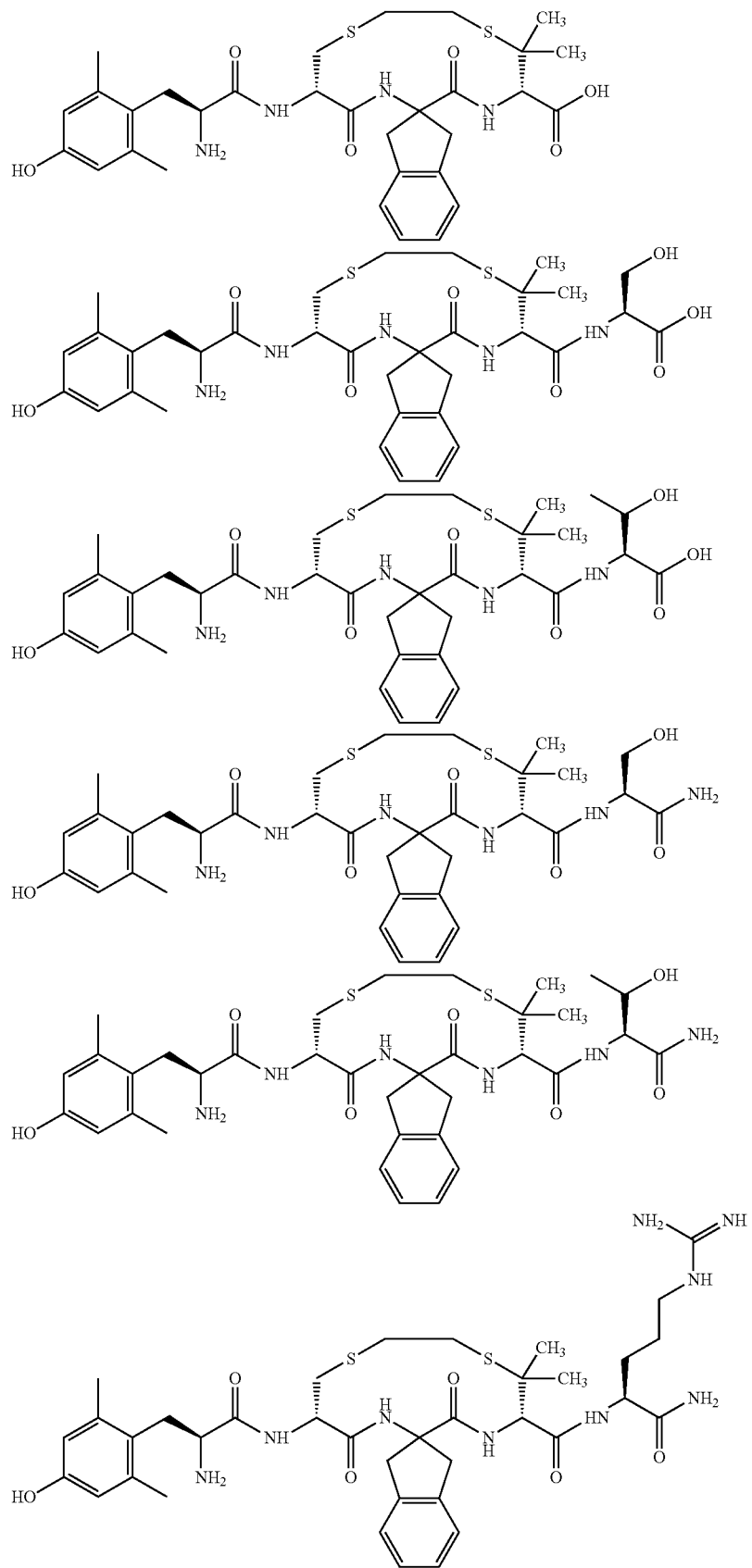

-continued

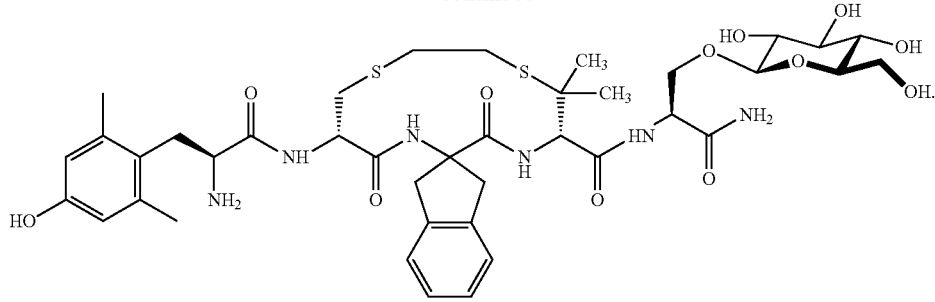

Optionally, the peptide increases the half life of the compound. Half life can be increased by, e.g., increasing the molecular weight of the compound to avoid renal clearance and/or incorporating a ligand for the nFc receptor-mediated recycling pathway. In one embodiment, the peptide is an albumin fragment (e.g., human serum albumin (HSA) or bovine serum albumin (BSA)), an albumin binding domain, a proline-alanine-serine multimer (PASylation), or an antibody fragment (e.g., an Fc portion of an antibody).

A cell penetrating peptide (CPP) also is a contemplated substituent at $R^1$ and/or X. CPPs are also known in the art as protein transduction domains, membrane translocating sequences, and Trojan peptides. CPPs are short peptides, typically comprising no more than 40 amino acids, with enhanced ability to traverse the plasma membrane and deliver cargo to the interior of almost any cell. CPPs tend to be cationic and rich in arginine and lysine amino acids. Examples of CPPs include HIV TAT, the third alpha-helix of Antennapedia homeodomain protein, HSV VP22, polyproline sweet-arrow peptide, transportan, polyarginine, polylysine, and peptides derived from calcitonin, buforin I, and SynB. CPPs are further described in, e.g., Delcroix et al., *Pharmaceuticals* 2010; 3(3):448-470; Sebbage, *Bioscience Horizons* 2009; 2(1):64-72; and Morris et al., *Biol. Cell.* 2008; 100:201-217.

The invention further includes compounds of formula (I) conjugated (chemically linked) to an entity that confers a benefit to the compound such as, for example, e.g., enhanced half life, enhanced solubility, enhanced stability, enhanced cellular uptake, enhanced transport across the blood-brain barrier, means of detection, or additional therapeutic property. Suitable entities include the peptides described above with respect to $R^1$ and X of formula (I). For example, in various aspects, the compound is conjugated to albumin, an antibody or fragment thereof (e.g., an Fc portion of an antibody), a proline-alanine-serine multimer (PASylation), or a CPP. Alternative entities for conjugation to the compound include, but are not limited to, a dye, a fluorescence dye, a radionuclide, and a radionuclide-containing complex.

The compounds of formula (I), if desired, are conjugated to one or more water soluble polymers. Exemplary polymers include, but are not limited to, polyethylene glycol (PEG), polyoxyethylene glycol, polypropylene glycol, monomethoxy-polyethylene glycol, dextran, hydroxyethyl starch, cellulose, poly-(N-vinyl pyrrolidone)-polyethylene glycol, propylene glycol homopolymers, a polypropylene oxide/ethylene oxide co-polymer, polysialic acid (PSA), polyoxyethylated polyols (e.g., glycerol) and polyvinyl alcohol, as well as mixtures of any of the foregoing. In one aspect, the compound is conjugated to a PEG moiety. PEG moieties are available in different shapes (e.g., linear or branched) and different sizes (e.g., 40 kD, 30 kD, 20 kD, 10 kD, 5 kD, or 1 kD in size). For further discussion of water soluble polymer attachments, see U.S. Pat. Nos. 4,640,835; 4,496,689; 4,301,144; 4,670,417; 4,791,192; and 4,179,337.

The invention also includes compounds of formula (I) conjugated to ligands that mediate receptor-mediated transcytosis for transport across the blood-brain barrier. Examples of receptor-mediated transcytosis targets include, e.g., the transferrin receptor, the insulin receptor, low density lipoprotein receptor-related proteins 1 and 2, and the diphtheria toxin receptor. Ligands to the receptors and methods of conjugating ligands to therapeutic cargo are known in the art and described in, e.g., Jones & Shusta, *Pharm. Res.* 2007; 24(9): 1759-1771.

The compounds of the invention are made in a variety of ways. In one aspect, the compounds are synthesized by solid phase synthesis techniques including those described in Merrifield, *J. Am. Chem. Soc.* 1963; 85:2149; Davis et al., *Biochem. Intl.* 1985; 10:394-414; Larsen et al., *J. Am. Chem. Soc.* 1993; 115:6247; Smith et al., *J. Peptide Protein Res.* 1994; 44:183; O'Donnell et al., *J. Am. Chem. Soc.* 1996; 118:6070; Stewart and Young, *Solid Phase Peptide Synthesis*, Freeman (1969); Finn et al., *The Proteins,* 3rd ed., vol. 2, pp. 105-253 (1976); and Erickson et al., *The Proteins,* 3rd ed., vol. 2, pp. 257-527 (1976).

The compounds of the invention bind MOR and DOR, optionally demonstrating substantially equivalent binding affinity for both receptors. Binding affinities differing by no more than 10-fold (e.g., no more than 5-fold) are "substantially equivalent" binding affinities. The compounds also, in various embodiments, selectively bind MOR and DOR, exhibiting decreased affinity for kappa-opioid receptor (KOR). In this regard, the compounds optionally bind MOR and DOR with a binding affinity at least 100 times (e.g., at least 250 times, at least 300 times, at least 400 times, or at least 500 times) greater than the compound binds KOR. Binding affinity is measured using any suitable technique, such as the competitive binding assays described in the Example; Przydzial et al., *J. Pept. Res.* 2005; 65(3):333-42; Balboni et al., *J. Med. Chem.* 2002; 45:5556-5563; Lazarus et al., *J. Med. Chem.* 1991; 34:1350-1359; Salvadori et al., *J. Med. Chem.* 1999; 42:5010-5019; and Balboni et al., *Bioorg. Med. Chem.* 2003; 11:5435-5441. Alternative techniques for evaluating binding to MOR or DOR include, for example, flow cytometry, immunofluorescence microscopy, immunoelectron microscopy, and confocal laser microscopy. See, for example, U.S. Pat. No. 4,661,913, and Cechetto et al., *Exp Cell Res.* 2000; 260:30-39. In this regard, the invention also includes a method of detecting MOR and/or DOR in a biological sample, the method comprising contacting the sample with the inventive compound and detecting binding of the compound to MOR and/or DOR in the sample. In various embodiments, the method comprises exposing the sample to the compound, washing excess compound from the sample, and determining the presence or absence of compound bound to MOR and/or DOR. Optionally, the compound is conjugated to a detection moiety (e.g., marker protein, radiolabel, and the like) to facilitate detection of the compound.

The inventive compounds are bifunctional opioid receptor modulators. The compounds are MOR agonists, i.e., the compounds trigger or upregulate MOR-mediated biological activity, such as analgesia. Additionally, the compounds are DOR antagonists, i.e., the compounds inhibit or prevent one or more of DOR's biological activities (such as development of dependence, gastrointestinal motility, or cardiovascular regulation) in response to a DOR agonist. MOR agonism and DOR antagonism is determined using any suitable assay, including assays that detect up- or down-regulation of G protein mediated signal transduction pathways associated with the opioid receptors. An exemplary assay is described in the Example, and entails measurement of radioactive GTP analogs produced by activated G proteins. Agonism is generally described in terms of potency, i.e., the concentration of compound required to achieve a 50% increase in G protein activity (and, by extension, opioid receptor activity). Agonism also generally described in terms of efficacy, i.e., the maximum level of G protein activity triggered by the compound. Efficacy often is reported as a percentage of the level of activity achieved by a "standard" receptor agonist (for example, DAMGO ([D-Ala$^2$,N-MePhe$^4$,Gly-ol]-enkephalin) for MOR or DPDPE ([D-Pen$^2$,D-Pen$^5$]-enkephalin) for DOR). Optionally, the inventive compound enhances MOR-mediated G protein activation with a half maximal effective concentration (EC50) of less than or equal to $1\times10^{-7}$ M, less than or equal to $1\times10^{-8}$ M, less than or equal to $1\times10^{-9}$ M, or less than or equal to $1\times10^{-10}$ M. A compound of formula (I), in various embodiments, provides at least 10% max. stimulation of MOR (e.g., at least 15%, at least 20%, at least 25%, at least 30%, at least 35%, at least 40%, at least 50%, at least 55%, or at least 60% max. stimulation of MOR) in the [$^{35}$S] GTPγS stimulation assay described in the Example. In one aspect, the compound exhibits MOR agonism efficacy similar to that of morphine (e.g., the compound's % max. in the [$^{35}$S]GTPγS stimulation assay described in the Example is within 10% of the % max. calculated for morphine). Optionally, the compound is more potent at MOR-coupled G protein stimulation than morphine and/or endomorphin (e.g., 10-fold, 20-fold, 30-fold, or 40-fold more potent than morphine measured using the [$^{35}$S]GTPγS stimulation assay described in the Example). A DOR antagonist does not activate G proteins itself and inhibits G protein activation by at least one DOR agonist. A DOR antagonist also preferably counteracts (i.e., reverses, lessens, or prevents) DOR agonist-mediated inhibition of forskolin-stimulated adenylyl cyclase.

Additional examples of techniques for examining agonist and/or antagonist activity of a compound include, but are not limited to, the mouse vas deferens (MVD) bioassay of DOR bioactivity and the guinea pig ileum (GPI) bioassay of MOR activity, both of which are described in Sasaki et al., *Bioorg. Med. Chem.* 2003; 11:675-678 and U.S. Patent Application Publication No. 20080269143. In vivo models for evaluating opioid receptor activity in response to opioid receptor modulators include but are not limited to, the tail flick test (Harris et al., *J. Pharmacol. Meth.* 1988; 20:103-108; and Sing et al., P.A. Amber (v. 3.0. rev. A), Dept. Pharm. Chem., University of California, San Francisco (1988)) and the hot-plate test (see, e.g., Woolfe et al., *J. Pharmacol. Exp. Ther.* 1944; 80:300-307).

Any of the compounds of the invention also is provided in a composition (e.g., a pharmaceutical composition). In this regard, the compound is formulated with a physiologically-acceptable (i.e., pharmacologically-acceptable) carrier, buffer, excipient, or diluent, as described further herein. Optionally, the compound is in the form of a physiologically acceptable salt, ester, or solvate, which is encompassed by the invention. "Physiologically acceptable salts" means any salts that are pharmaceutically acceptable. Some examples of appropriate salts include acetate, hydrochloride, hydrobromide, sulfate, citrate, tartrate, glycolate, and oxalate. If desired, the composition comprises one or more additional pharmaceutically-effective agents.

The invention further includes a method of modulating MOR and/or DOR receptor activity. The method comprises exposing a MOR and/or a DOR to the compound described herein. Also provided is a method for treating a MOR mediated disorder in a subject, a method for treating a DOR mediated disorder in a subject, and a method for treating a MOR mediated disorder and a DOR mediated disorder in a subject. In various embodiments, the MOR mediated disorder is a disorder alleviated by a MOR agonist, and the DOR mediated disorder is a disorder alleviated by a DOR antagonist. The method comprises administering to a subject in need thereof the composition comprising the inventive compound in an amount sufficient to ameliorate the disorder. Disorders associated with MOR include, but are not limited to, pain and gastrointestinal motility disorders (e.g., constipation). Disorders associated with DOR include, but are not limited to, seizures and depression. See, e.g., Jutkiewicz et al., *J. Pharmacol. Exp. Ther.* 2006; 317(3):1337-48;Clapp et al. *Am. J. Obstet. Gynecol.* 1998; 178(2):397-401; Nielsen et al., *Biol Psychiatry.* 2008; 64(11):974-81; and Hubbell et al., *Experimental and Clinical Psychopharmacology* 1995; 3(2):123-128.

Additionally, the invention provides a method of treating pain in a subject, the method comprising administering to the subject a composition comprising the inventive compound in an amount sufficient to induce analgesia. "Pain" is generally described in terms of duration, cause, and/or afflicted region of the body. The invention includes treatment of any type of pain, including neuropathic pain and nociceptive pain. Additional examples of pain include, but are not limited to, visceral pain, muscle pain, inflammatory pain, colicky pain, referred pain, and idiopathic pain. The method further includes treatment of, e.g., long term persistent pain, chronic pain, breakthrough pain, subacute pain, and acute pain. Acute pain is generally a self-limiting physiological response to a discrete bodily insult (e.g., inflammation, surgery, bone fracture, headache, sprain, strains, burn, or chemical exposure). Chronic pain persists longer than would be expected for healing from a discrete bodily insult, and includes disorders such as, e.g., back pain, myofascial pain, arthritis, cancer pain, neuropathic pain, and fibromyalgia.

Efficacy in treating (i.e., reducing, easing, suppressing, or alleviating) pain in a subject in need thereof is determined using any suitable method. Analgesic efficacy is measured, for example, using a nociception assay in animals such as a tail withdrawal test, pain relief score, or a pain intensity difference score, optionally recorded at a given time point, or over time, or as compared to a baseline, and includes calculations based on area under the curve such as those plotting Total Pain Relief Score (TOTPAR) or the Sum of Pain Intensity Difference (SPID), as described in the Handbook of Pain Assessment, 2d. Turk & Meldzack, Eds., The Guilford Press, New York, N.Y. (2001). Increases in time to re-medication and increases in quality of life measurements also are indicators of successful pain treatment.

The inventive compound is advantageous for the treatment of pain requiring long term administration of opioid receptor agonists, which is connected to an increased risk of adverse side effects. The incidence and/or intensity of adverse side effects associated with opioid use are attenuated with use of the inventive compounds compared to monofunctional opioids, such as morphine. Examples of adverse excitatory effects include, without limitation, anti-analgesia, physical or psychological dependence, psychological dependence, tolerance, constipation, nausea, respiratory depression, sedation, and vomiting. Physical dependence is marked by physiologic adaptation to a drug that may ultimately lead to withdrawal symptoms when the drug is discontinued. "Tolerance" refers to circumstances where dosage must be increased in order to maintain the physiological response to the agonist achieved at the beginning of treatment.

"Treating" pain or an opioid receptor-associated disorder does not require a 100% abolition of pain or the disorder. Any decrease in pain sensation or symptoms of the disorder constitutes a beneficial biological effect in a subject. In this regard, the invention reduces pain or the symptoms of a MOR associated disorder and/or a DOR associated disorder by, e.g., at least about 5%, at least about 10% or at least about 20% compared to levels of, e.g., pain observed in the absence of the inventive method (e.g., in a biologically-matched control subject, subject that is not administered the inventive compound, or the subject administered the compound prior to treatment). In some embodiments, pain is reduced by at least about 30%, at least about 40%, at least about 50%, or at least about 60%. In some embodiments, the inventive method inhibits pain by at least about 70%, at least about 80%, at least about 90%, or more (about 100%) compared to that experienced in the absence of the inventive method.

A particular administration regimen for a particular subject will depend, in part, upon the compound, the amount of compound administered, the route of administration, and the cause and extent of any side effects. The amount of compound administered to a subject (e.g., a mammal, such as a human) in accordance with the invention should be sufficient to effect the desired response over a reasonable time frame. Dosage typically depends upon the route, timing, and frequency of administration. Accordingly, the clinician titers the dosage and modifies the route of administration to obtain the optimal therapeutic effect, and conventional range-finding techniques are known to those of ordinary skill in the art.

In the inventive method of treating pain in a subject, the composition comprising the inventive compound is administered in an amount to induce analgesia. Put another way, the dose of composition administered is sufficient to reduce, ease, suppress, or alleviate pain. Purely by way of illustration, the inventive method comprises administering, e.g., from about 0.1 µg/kg up to about 100 mg/kg of compound or more, depending on the factors mentioned above. In other embodiments, the dosage ranges from 1 µg/kg up to about 100 mg/kg; or 5 µg/kg up to about 100 mg/kg; or 10 µg/kg up to about 100 mg/kg. Some conditions require prolonged treatment, which may or may not entail administering lower doses of compound over multiple administrations. If desired, a dose of the compound is administered as two, three, four, five, six or more sub-doses administered separately at appropriate intervals throughout the day, optionally, in unit dosage forms. The treatment period will depend on the particular condition and type of pain, and may last one day to several months.

Suitable methods of administering a physiologically-acceptable composition, such as a pharmaceutical composition comprising the inventive compound, are well known in the art. Although more than one route can be used to administer a compound, a particular route can provide a more immediate and more effective reaction than another route. Depending on the circumstances, a pharmaceutical composition comprising the compound is applied or instilled into body cavities, absorbed through the skin or mucous membranes, ingested, inhaled, and/or introduced into circulation. For example, in certain circumstances, it will be desirable to deliver a pharmaceutical composition comprising the agent orally, through injection by intravenous, intraperitoneal, intracerebral (intraparenchymal), intracerebroventricular, intramuscular, intraocular, intraarterial, intraportal, intralesional, intramedullary, intrathecal, intraventricular, transdermal, subcutaneous, intraperitoneal, intranasal, enteral, topical, sublingual, urethral, vaginal, or rectal means, by sustained release systems, or by implantation devices. If desired, the compound is administered regionally via intrathecal administration, intracerebral (intra-parenchymal) administration, intracerebroventricular administration, or intraarterial or intravenous administration feeding the region of interest. Alternatively, the composition is administered locally via implantation of a membrane, sponge, or another appropriate material onto which the desired compound has been absorbed or encapsulated. Where an implantation device is used, the device is, in one aspect, implanted into any suitable tissue or organ, and delivery of the desired compound is, for example, via diffusion, timed-release bolus, or continuous administration.

To facilitate administration, the compound is, in various aspects, formulated into a physiologically-acceptable composition comprising a carrier (i.e., vehicle, adjuvant, or diluent). The particular carrier employed is limited only by chemico-physical considerations, such as solubility and lack of reactivity with the compound, and by the route of administration. Physiologically-acceptable carriers are well known in the art. Illustrative pharmaceutical forms suitable for injectable use include sterile aqueous solutions or dispersions and sterile powders for the extemporaneous preparation of sterile injectable solutions or dispersions (for example, see U.S. Pat. No. 5,466,468). Injectable formulations are further described in, e.g., Pharmaceutics and Pharmacy Practice, J. B. Lippincott Co., Philadelphia. Pa., Banker and Chalmers. eds., pages 238-250 (1982), and ASHP Handbook on Injectable Drugs, Toissel, 4th ed., pages 622-630 (1986)). A pharmaceutical composition comprising the inventive compound is, in one aspect, placed within containers, along with packaging material that provides instructions regarding the use of such pharmaceutical compositions. Generally, such instructions include a tangible expression describing the reagent concentration, as well as, in certain embodiments, relative amounts of excipient ingredients or diluents (e.g., water, saline or PBS) that may be necessary to reconstitute the pharmaceutical composition.

When appropriate, the compound is administered in combination with other substances (e.g., therapeutics) and/or other therapeutic modalities to achieve an additional (or augmented) biological effect. These other therapeutics/co-treatments include, for example, surgery, radiation treatment, chemotherapy, anti-angiogenic factors (for instance, soluble growth factor receptors (e.g., sflt), growth factor antagonists (e.g., angiotensin), etc.), antibiotics, hormone therapy, anti-inflammatory agents (e.g., Non-Steroidal Anti-Inflammatory Drugs (NSAIDs) or steroidal anti-inflammatory substances), antiviral agents, anti-bacterial agents, cough suppressant, decongestant, or expectorant, pain relievers, and the like. Optionally, the compound is administered in combination with an agent that facilitates transport across the blood-brain barrier and/or an agent that blocks efflux from the brain.

Additional combination therapies not specifically listed herein are also within the scope of the present invention.

The invention thus includes administering to a subject the inventive compound in combination with one or more additionally suitable substances(s), each being administered according to a regimen suitable for that medicament. This aspect includes concurrent administration (i.e., substantially simultaneous administration) and non-concurrent administration (i.e., administration at different times, in any order, whether overlapping or not) of the agent and one or more additionally suitable agents(s). It will be appreciated that different components are, in certain aspects, administered in the same or in separate compositions, and by the same or different routes of administration.

The invention, thus generally described, will be understood more readily by reference to the following example, which is provided by way of illustration and is not intended to limit the invention.

EXAMPLE

This example describes the production and confirmation of the bifunctional opioid receptor actions of exemplary compounds of formula (I), depicted in FIG. 1.

Materials and Methods

Materials: Fmoc-protected amino acids were obtained from Advanced ChemTech (Louisville, Ky., USA) or Sigma-Aldrich (St. Louis, Mo., USA). All other reagents for compound synthesis and characterization were from Sigma-Aldrich unless otherwise indicated. Fetal bovine serum, cell culture media and additives were purchased from Gibco Life Sciences (Grand Island, N.Y., USA). [D-Ala$^2$, N-Me-Phe$^4$, Gly$^5$-ol]-enkephalin (DAMGO) and other biochemicals were obtained from Sigma-Aldrich. [$^{35}$S]-guanosine-5'-O-(3-thio) triphosphate ([$^{35}$S]-GTPγS; 1250Ci (46.2TBq)/mmol) and [$^3$H]-diprenorphine were purchased from Perkin Elmer (Boston, Mass., USA).

Solid Phase Compound Synthesis and Cyclization: Compounds were synthesized by solid phase methods on an ABI Model 431A solid phase peptide synthesizer (Applied Biosystems, Foster City, Calif., USA) as previously described (Purington et al., *J. Med. Chem.* 2009; 52(23):7724-7731). Rink resin (Advanced ChemTech) was used as the solid support for C-terminal carboxamide peptides and Wang resin conjugated with D-Pen (Advanced ChemTech) for C-terminal carboxylic acid peptides. Peptide elongation on the resin was performed by treating resin with piperidine (Sigma-Aldrich) to cleave the Fmoc-protecting group and diisopropylethylamine (DIEA) activation. This was followed by coupling of the next amino acid with o-benzotriazol-1-yl-N,N,N',N'-tetramethyl uronium hexafluorophosphate (HBTU) and 1-hydroxybenzotriazole (HOBt; Applied Biosystems). These steps were repeated until the entire peptide sequence was assembled. A trifluoroacetic acid/H$_2$O/tri-isopropylsilane solution (9:0.5:0.5, v/v/v) was used to cleave the peptide from the resin and simultaneously remove all side chain-protecting groups. The compound in solution was filtered and subjected to semi-preparative reverse phase high-performance liquid chromatography (RP-HPLC) to afford the linear disulfhydryl-containing peptide. Linear peptide confirmation was obtained by liquid chromatography-mass spectroscopy (LC-MS) (Agilent Technologies; Santa Clara, Calif., USA).

Ethylene Dithioether Cyclization: To form ethylene dithioether-containing cyclic peptides (Purington et al., *J. Med. Chem.* 2009; 52(23):7724-7731), linear disulfhydryl peptide was added to dimethylformamide (DMF) and maintained at 5° C. under a N$_2$ atmosphere (0.1 mg linear peptide/ml DMF). Approximately 10 Eq of potassium t-butoxide was added to the peptide solution, followed by the addition of 10 Eq of dibromoethane. The reaction was quenched with 5 mL AcOH after 2 hours and the solvent removed in vacuo. The residue was dissolved in water, filtered, and subjected to semi-preparative RP-HPLC to obtain the ethylene dithioether cyclized peptide compound.

Glycosylation: In order to incorporate the glycosylated moiety into the peptide, L-Serine-OBn was glycosylated and used as a building block in the solid phase peptide synthesis. The glycosylated amino acid was synthesized starting with the protection of L-Ser-OBn with Fmoc-Cl, followed by the microwave glycosylation with β-glucose peracetate using InBr$_3$ as the Lewis acid promotor and the Discover® CEM Microwave, holding the temperature at 80° C. for 5 minutes. The reaction was monitored by thin layer chromatography. Without further purification, the benzyl ester protecting group was cleaved under hydrogenolysis conditions with Pd/C 10%, 10 psi H$_2$. The crude material from the hydrogenolysis was purified by silica gel column using ethyl acetate to remove impurities and eluting the final desired Fmoc-L-serine-β-O-glucose peracetate with methanol. If analysis indicated the presence of Fmoc-L-serine, the desired glycosylated counterpart was purified one final time by column chromatography using 95:5:0.1 DCM/MeOH/AcOH as the mobile phase. Analysis and confirmation of the final product included NMR spectroscopy and HPLC. The glycosylated amino acid was then used in the peptide synthesis as described above. The acetate groups were removed from the final peptide on the resin, prior to cleavage, using a solution of 4:1 hydrazine monohydrate to methanol, twice for 30 minutes and one final time for 1 hour.

Characterization of Compounds: All final product compounds were >97% pure as assessed by analytical RP-HPLC on a Vydac® 218TP C-18 column (The Nest Group, Southboro, Mass.) using the solvent system 0.1% trifluoroacetic acid (TFA) in water/0.1% TFA in acetonitrile by a gradient of 0-70% organic component in 70 minutes, monitored at 230 nm. Compounds displayed the appropriate molecular weights as determined by LC-MS.

Cell Lines and Membrane Preparations: C6-rat glioma cells stably transfected with a rat mu (C6-MOR) or rat delta (C6-DOR) opioid receptor (Lee et al., *Eur J Pharmacol* 1999; 378(3):323-330) and Chinese hamster ovary (CHO) cells stably expressing a human kappa (CHO-KOR) opioid receptor (Husbands et al., *Eur J Pharmacol* 2005; 509(2-3):117-125) were used for all in vitro assays. Cells were grown to confluence at 37° C. in 5% CO$_2$ in either Dulbecco's Modified Eagle's Medium (DMEM; C6 cells), or DMEM-F12 Medium (CHO cells) containing 10% fetal bovine serum and 5% penicillin-streptomycin. Membranes were prepared by washing confluent cells three times with phosphate-buffered saline (0.9% NaCl; 0.61 mM Na$_2$HPO$_4$; and 0.38 mM KH$_2$PO$_4$, pH 7.4). Cells were detached from the plates by incubation in harvesting buffer (20 mM HEPES, pH 7.4; 150 mM NaCl; and 0.68 mM EDTA) and pelleted by centrifugation at 200×g for 3 minutes. The cell pellet was suspended in ice-cold 50 mM Tris-HCl buffer, pH 7.4 and homogenized with a Tissue Tearor™ (Biospec Products, Inc., Bartlesville, Okla., USA) for 20 seconds at setting 4. The homogenate was centrifuged at 20,000×g for 20 minutes at 4° C. and the pellet re-homogenized in 50 mM Tris-HCl with a Tissue Tearor™ for 10 seconds at setting 2, followed by re-centrifugation. The final pellet was re-suspended in 50 mM Tris-HCl, to 0.5-1.0 mg/ml protein and frozen in aliquots at −80° C. (Clark et al., *J Biol Chem* 2003; 3278(11):9418-9425). Protein concentration was determined using the BCA protein assay (Thermo Fisher Scientific, Rockford, Ill., USA) using bovine serum albumin as the standard.

Radioligand Binding Assays: Opioid ligand-binding assays (Przydzial et al., *J Pept Res* 2005; 65(3):333-342) were performed using competitive displacement of 0.2 nM [$^3$H] diprenorphine by the test compound from membrane preparations containing opioid receptors. The assay mixture, containing membrane suspension (20-40 µg protein/tube) in 50 mM Tris-HCl buffer (pH 7.4), [$^3$H]diprenorphine, and various concentrations of compound was incubated at 25° C. for 1 hour to allow binding to reach equilibrium. The samples were rapidly filtered through GF/C filters (Whatman, Middlesex, UK) using a Brandel harvester and washed three times with 50 mM Tris-HCl buffer. The radioactivity retained on dried filters was determined by liquid scintillation counting after saturation with EcoLume™ liquid scintillation cocktail (MP Biomedicals, Solon, Ohio, USA) in a Wallac 1450 MicroBeta® (Perkin Elmer). Non-specific binding was determined using 10 µM naloxone. $K_i$ values were calculated using nonlinear regression analysis to fit a logistic equation to the competition data using GraphPad Prism version 5.01 for Windows (GraphPad Software, La Jolla, Calif., USA). The results presented are the mean±standard error from at least three separate assays performed in duplicate.

[$^{35}$S]GTP γS Binding Assay: Agonist stimulation of [$^{35}$S]GTPγS binding was measured as described previously (Traynor et al., *Mol Pharmacol* 1995; 47(4):848-854). Briefly, membranes (20-40 µg of protein/tube) were incubated 1 hour at 25° C. in GTPγS buffer (50 mM Tris-HCl, pH 7.4; 100 mM NaCl; and 5 mM $MgCl_2$) containing 0.1 nM [$^{35}$S]GTPγS, 100 µM GDP, and varying concentrations (0.001-10,000 nM) of compounds. Compound stimulation of [$^{35}$S]GTPγS was compared with 10 µM standard compounds DAMGO, DPDPE, or U69,593. The reaction was terminated by rapidly filtering through GF/C filters, washing three times with GTPγS buffer and retained radioactivity measured as described above. Experiments were performed at least three times in duplicate and $EC_{50}$ values determined using nonlinear regression analysis with GraphPad Prism. To determine antagonist properties of compounds at DOR, [$^{35}$S]GTPγS binding was determined for DPDPE in the presence or absence of a single concentration of peptide (Kosterlitz et al., *Br J Pharmacol Chemother* 1968; 33(2):266-276). The $EC_{50}$ value in the presence of compound was divided by the $EC_{50}$ value for DPDPE alone, and this ratio (DR) was employed to calculate the $K_e$ value using the equation $K_e$=[antagonist]/(DR-1).

Whole Cell Acute Inhibition of Adenylyl Cyclase: Inhibition of adenylyl cyclase by opioid standards or compounds was measured in C6-DOR cells grown to confluence in 96-well plates. Cells were washed in serum-free DMEM at least 30 minutes prior to the start of the assay and incubated with various concentrations (1-1000 nM) of DPDPE or compound in serum-free media containing 5 µM forskolin (FSK) and 0.25 mM 3-isobutyl-1-methylxanthine (IBMX) for 30 minutes at 37° C. The assay was quenched during a 30-minute incubation at 4° C. by replacing media with 0.1 mL lysis buffer (0.3% Tween-20, 5 µM HEPES in $dH_2O$, pH 7.4). Cyclic AMP (cAMP) was measured from samples in a 384-well plate with a BioTek MultiMode Microplate Reader (Winooski, Vt., USA) using the AlphaScreen® cAMP detection kit (Perkin Elmer) according to manufacturer's instructions. Inhibition of cAMP accumulation was calculated as a percent of FSK-stimulated cAMP accumulation in vehicle-treated cells. $EC_{50}$ values were calculated for each compound using GraphPad Prism. Experiments were performed in triplicate and repeated a minimum of three times.

Cell Permeability Assay: Caco-2 cells at a passage line of 21 were seeded at a density of $0.3\times10^5$ cells/well on untreated culture inserts of polycarbonate membrane with 0.4 µm pores and a surface area of 1.12 $cm^2$. The culture inserts containing the Caco-2 cells were placed in a 12 transwell plate. The DMEM, high glucose culture medium, supplemented with 10% FBS, was generally changed every other day. Transport studies were performed 21 days after seeding upon full differentiation and the TEER values were stable at 500-600Ω $cm^2$. The study of transport from apical to basolateral was initiated by removal of medium from both sides of the monolayer and replacement with apical buffer, pH 6.4 (500 µL) and basolateral buffer, pH 7.4 (1500 µL), both warmed to 37° C. The cells were incubated for 15 minutes at 37° C., 5% $CO_2$. The buffers were then removed and replaced with 500 µL 100 µM peptide in apical buffer on the apical side and 1500 µL basolateral buffer on the basolateral side, both prewarmed to 37° C. For the duration of the experiment, cells were kept at 37° C. except during the 100 µL sample removal from the basolateral side at predetermined times (15, 30, 45, 60, 75, 90 minutes). The samples were added to 200 µL 0.1% TFA in acetonitrile, and 100 µL of basolateral buffer was added to the basolateral side of the monolayer. Apical samples of 10 µL were removed at 60 and 90 minutes. Samples were analyzed by HPLC.

Nociception Assay: Mice were restrained in a clear cylindrical plastic container that permitted the tail to protrude and move freely. Approximately one inch of the tail tip was immersed in warm water (50±1° C.), and the latency to tail withdrawal or tail flick was measured using a stopwatch. A cut-off latency of 20 seconds was used to prevent tissue damage. A baseline withdrawal latency was determined 30 minutes after an injection of saline or vehicle solution. A cumulative dosing procedure was used in which a cumulative dose was administered every 30 minutes, and the withdrawal latency was evaluated 30 minutes after each injection. All vehicle and drug doses were given by intraperitoneal injection. The average withdrawal latency per dose for the test group was determined. The individual percent maximum possible effect (% MPE) was calculated as % MPE=[(individual test latency)−(individual baseline latency)/(cutoff latency−individual baseline latency)]×100.

Statistical Analysis: Data were analyzed using Student's two-tailed t test or analysis of variance followed by Bonferroni's post-hoc test using GraphPad Prism where appropriate. A p value less than 0.05 was used to determine significance.

Results

Compounds were synthesized using solid-phase methodology and purified by high performance liquid chromatography (HPLC). The binding affinity of each compound for three opioid receptors was determined and compared to the binding affinity of JOM-6 and DIPP(Ψ)$NH_2$. Affinity was determined by non-linear regression following displacement of 0.2 nM [$^3$H]diprenorphine from membrane preparations of opioid receptors individually expressed in C6-rat glioma (MOR and DOR) or Chinese hamster ovary cells (KOR). The results are provided in FIG. 2 and FIG. 4, and are reported as mean $K_i$±standard error from at least three experiments performed in duplicate.

The ability of the compounds to activate G protein at each receptor was assessed using the [$^{35}$S]GTPγS stimulation assay. The experiments were performed in duplicate at least three times. The results are provided in FIG. 3 and FIG. 5, reported as the mean±standard error. $EC_{50}$ values were determined from non-linear regression analysis of [$^{35}$S]GTPγS incorporation. The [$^{35}$S]GTPγS results are reported as both efficacy for [$^{35}$S]GTPγS incorporation as a percentage of a known opioid receptor agonist ([D-Ala$^2$-N-Me-Phe$^4$-Gly$^5$-ol]-enkephalin (DAMGO) at MOR, D-Pen-2,5-enkephalin (DPDPE) at DOR, and U69,593 at KOR) and a calculated EC50 value. All compounds were compared to the previously developed MOR-selective peptide JOM-6 (Tyr-(S—CH2-CH2-S)-D-Cys-Phe-D-Pen-NH2) (McFadyen et al., 2000). Compound 2 and Compound VRP-26 underwent further analysis, as described below.

Opioid Receptor Binding

JOM-6 displays 100-fold MOR selectivity in binding to opioid receptors (0.3 nM±0.04 affinity at MOR and 25 nM±1.5 at DOR, FIG. 2). Replacing the Tyr1 residue with Dmt1 and Phe3 with Aci3 while maintaining similar ring size with ethylene dithioether cyclization (abbreviated S—CH2-CH2-S) produced compound 1. These alterations did not change the binding affinity to MOR (0.6 nM±0.1), but significantly increased affinity at DOR (0.9 nM±0.2, p<0.001) and at KOR. Compound 2 replaced the C-terminal carboxamide residue with an acid, which produced a 100-fold decrease in KOR affinity compared to compound 1. While replacement of the carboxamide for the carboxy acid in compound 2 did not appear to greatly alter the overall binding affinity profile, there was a decrease in affinity to both MOR and DOR (2.4 nM±0.7 at MOR, p<0.05 and 2.3 nM±0.5 at DOR) when compared to compound 1. VRP-13, VRP-15, VRP-19, VRP-21, and VRP-24 replaced the C-terminal amide NH$_2$ group of compound 1 with an amino acid. VRP-26 replaced the C-terminal amide NH$_2$ group of compound 1 with a glycosylated serine carboxamide. The opioid receptor binding affinities of VRP-13, VRP-15, VRP-19, VRP-21, VRP-24, and VRP-26 are depicted in FIG. 4.

DIPP(Ψ)NH$_2$ and Dmt-Tic-Gly-NH-Bzl were also analyzed for opioid receptor binding (FIG. 2). DIPP(Ψ)NH$_2$ bound equally well to MOR and DOR with affinity values of 0.4 nM±0.1 at MOR and 0.4 nM±0.04 at DOR, and demonstrated 10-fold selectivity for these receptors over KOR (3.9 nM±0.2). Dmt-Tic-Gly-NH-Bzl, on the other hand, was DOR-selective, with a binding affinity of 0.2 nM±0.06. Binding affinity to MOR was in the nM range (26 nM±8), and KOR affinity was reduced still further (128 nM±42).

Stimulation of G Protein

JOM-6 was reported to be a MOR agonist when compared to the opioid ligand fentanyl, with an EC50 of 2.93 nM±0.8 (McFadyen et al., *J Pharmacol Exp Ther* 2000; 295(3):960-966). MOR agonist efficacy of compounds 1 and 2 were determined compared to the peptide agonist DAMGO as the standard ligand (FIG. 3). Compounds 1 and 2 both behaved as partial agonists at MOR, giving maximal stimulations of 58%±8 and 59%±11 of 10 μM DAMGO, respectively. MOR agonist efficacy of compounds VRP-19, VRP-24, and VRP-26 were determined compared to the peptide agonist DAMGO as the standard ligand (FIG. 5). VRP-19, VRP-24, and VRP-26 behaved as partial agonists at MOR, giving maximal stimulations of 44±11, 37.1±11, and 54.4±6.8 of 10 μM DAMGO, respectively. In comparison, the clinically used analgesic morphine produced 57%±5 stimulation versus DAMGO. The EC50 for compound 1 was the lowest of the novel compounds analyzed (0.4 nM±0.02 versus 4.7 nM±0.7 for peptide 2, p<0.01), although both displayed similar efficacies. Reference ligands DIPP(Ψ)NH$_2$ and Dmt-Tic-Gly-NH-Bzl were also determined to be partial agonists at MOR in this assay, giving relative stimulations of 18%±1 and 7%±2 compared with DAMGO, respectively (FIG. 3). The EC50 for both peptides was in the nM range, with DIPP(Ψ)NH$_2$ having an EC50 of 5.7 nM±3.3 and Dmt-Tic-Gly-NH-Bzl displaying an EC50 of 1.4 nM±0.2.

Compounds 1 and 2, VRP-19, VRP-24, and VRP-26 were all either low efficacy partial agonists or produced no measureable G protein stimulation in the [$^{35}$S]GTPγS assay at DOR (FIGS. 3 and 5). Compound 1 had the highest efficacy of all ligands tested, yielding 37%±4 stimulation and having an EC50 value of 1.4 nM±0.4 compared to DOR peptide agonist DPDPE (Mosberg et al., *Life Sci* 1983; 33 Suppl: 447-450). No [$^{35}$S]GTPγS incorporation was observed even with a 10 μM concentration of compound 2 or VRP-26. In contrast, some small amount of G protein stimulation was detected using the reference peptides at DOR, with Dmt-Tic-Gly-NH-Bzl providing 21%±4 stimulation compared to DPDPE and DIPP(Ψ)NH$_2$ afforded 2%±2 stimulation, although this small stimulation may be within the error of detection for this assay. No EC50 could be calculated for Dmt-Tic-Gly-NH-Bzl for [$^{35}$S]GTPγS incorporation.

Although compounds 1 and 2 displayed relatively low binding affinity to KOR (FIG. 2), the ability to stimulate G protein at this receptor was also measured. Both were either low efficacy partial agonists with no stimulation greater than 10% of the standard U69,593 (compound 1; 3%±3) or displayed no G protein stimulation (compound 2) (FIG. 3). At KOR, DIPP(Ψ)NH$_2$ and Dmt-Tic-Gly-NH-Bzl were both agonists, providing 5%±1 (Dmt-Tic-Gly-NH-Bzl, EC50 not determined) or 125%±42 (DIPP(Ψ)NH$_2$; EC50: 11 nM±3) of the U69,593 measured G protein stimulation.

MOR Agonist/DOR Antagonist Properties of Compound 2

Figure 6:
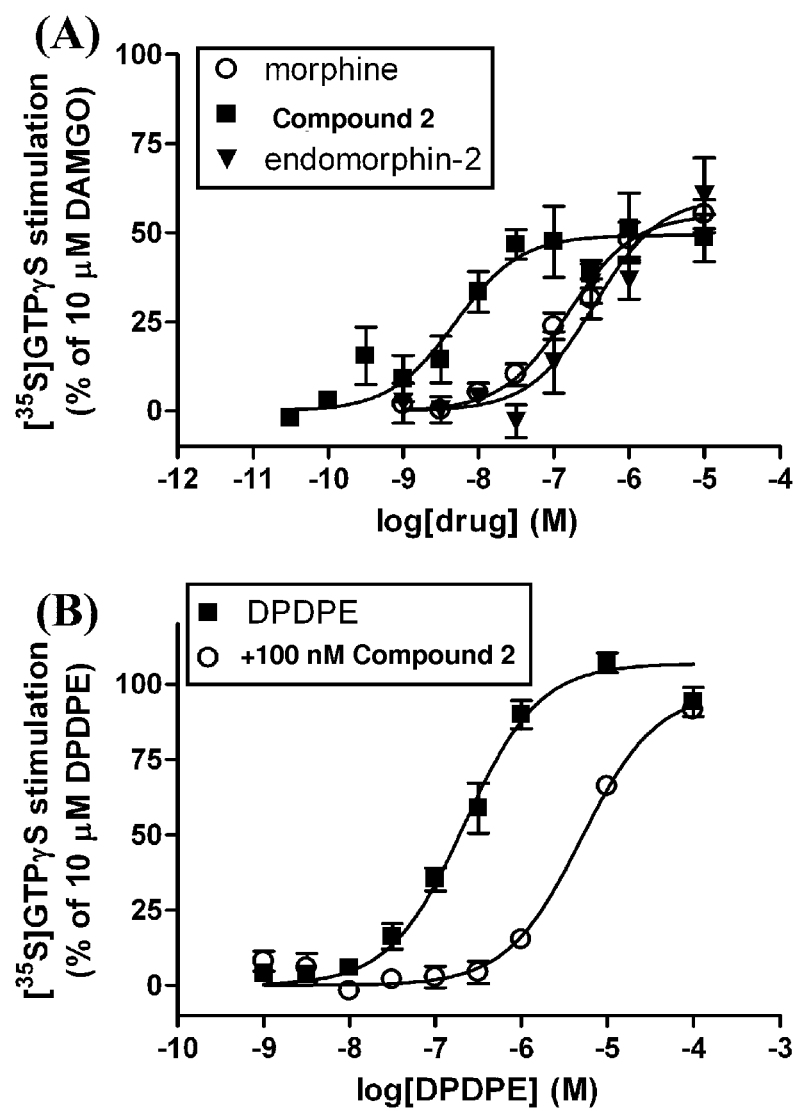
FIG. 6A is a line graph correlating compound concentration (x-axis; "log [drug] (M)") with the percent maximal MOR-associated G-protein stimulation obtained by the compound (y-axis; "[$^{35}$S]GTPγS stimulation").
FIG. 6B is a line graph correlating DPDPE concentration (x-axis; "log [DPDPE] (M)") with the percent maximal DOR-associated G-protein stimulation obtained by DPDPE in the absence and presence of compound 2 (100 nM) (y-axis; "[$^{35}$S]GTPγS stimulation"). The percent maximal values represent the percent of maximal G protein stimulation obtained with 10 μM DAMGO (FIG. 6A) or 10 μM DPDPE (FIG. 6B).

From the initial binding and efficacy results, compound 2 was chosen for further in vitro characterization. First, it was compared to the standard MOR agonists morphine and endomorphin-2 in its ability to elicit [$^{35}$S]GTPγS incorporation at MOR (FIGS. 3 and 6A). Compound 2 elicited 59%±11 stimulation compared to a 10 μM concentration of DAMGO. Similarly, morphine produced 57%±5 and endomorphin-2 gave 49%±7 stimulation. However, compound 2 was much more potent than either morphine or endomorphin-2 in the assay, displaying an EC50 of 4.1 nM±0.8 (p<0.001 compared to morphine, EC50 194 nM±21 and p<0.01 versus endomorphin-2, EC50 125 nM±31). At DOR, compound 2 behaved as an antagonist and was able to produce a rightward shift in the concentration-response curve for the standard DOR peptide agonist DPDPE (FIG. 6B). The EC50 for DPDPE was shifted from 246 nM±45 to 6300 nM±1000 upon the addition of 100 nM compound 2. This shift produced a calculated Ke value for antagonism of 4.4 nM±1.4.

Inhibition of Forskolin-Stimulated Adenylyl Cyclase

Figure 7:
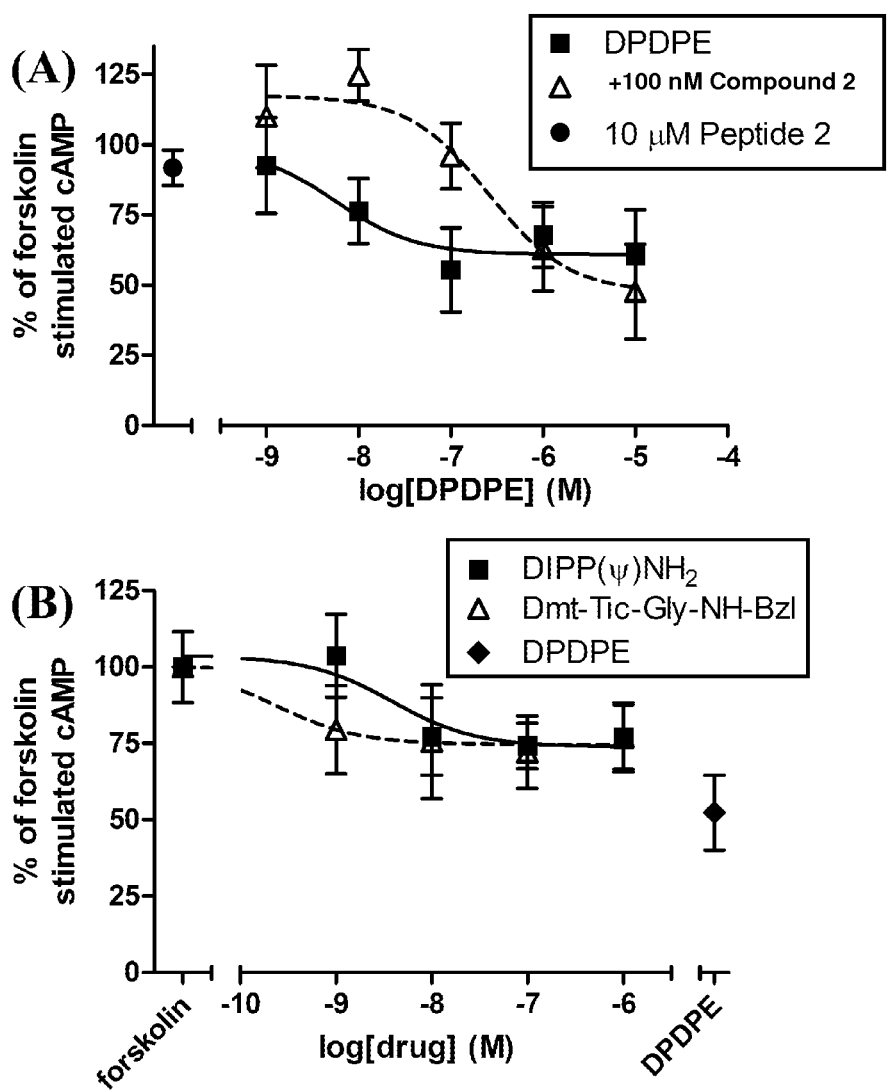
FIG. 7A is a line graph correlating DPDPE concentration (x-axis; "log [DPDPE] (M)") with the percent maximal forskolin-stimulated cAMP observed in the presence of compound (Peptide) 2 (10 μM) and DPDPE in the absence and presence of compound 2 (100 nM) (y-axis; "% of forskolin stimulated cAMP").
FIG. 7B is a line graph correlating compound concentration (x-axis; "log [drug] (M)") with the percent maximal forskolin-stimulated cAMP observed in the presence of DPDPE, Dmt-Tic-Gly-NH-Bzl, and DIPP(Ψ)NH$_2$ (y-axis; "% of forskolin stimulated cAMP"). DPDPE (1 mM) inhibited forskolin stimulation to 52%±12.
Figure 8:
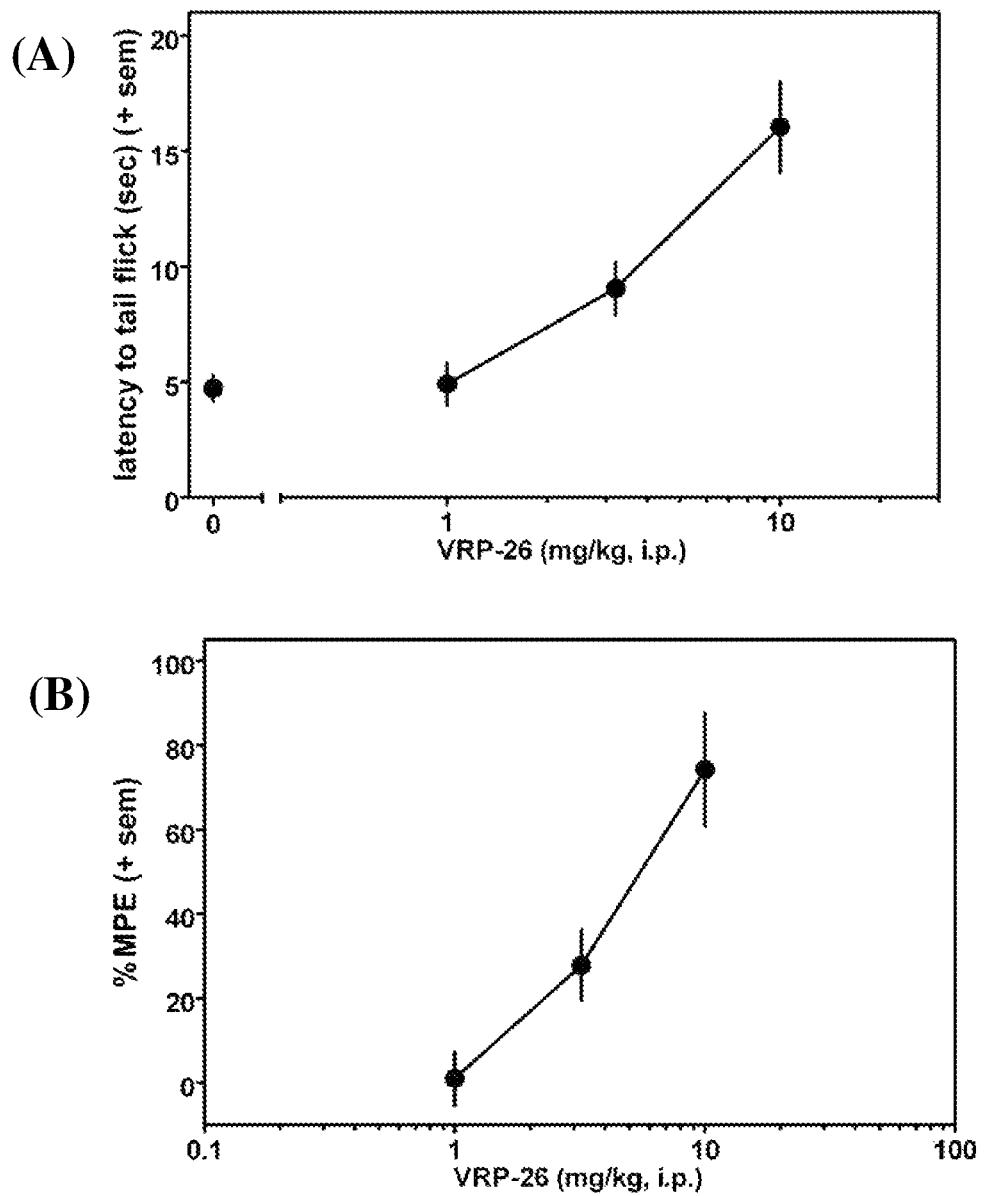
FIG. 8A is a line graph correlating VRP-26 treatment (x-axis; "VRP-26 (mg/kg, i.p.)") with the average tail withdrawal latency (y-axis; "latency to tail flick (sec) (+sem)").
FIG. 8B is a line graph correlating VRP-26 treatment (x-axis; "VRP-26 (mg/kg, i.p.)") with average percent maximum possible effect (y-axis; "% MPE (+sem)").

Due to amplification of signaling at downstream effectors, low efficacy agonists in producing [$^{35}$S]GTPγS incorporation were examined for the ability to inhibit adenylyl cyclase activity. This measure can aid in the determination of partial agonism or provide further evidence for an antagonist profile. Compound 2 maintained antagonist efficacy at downstream cellular effector adenylyl cyclase (FIG. 7A). Using a whole cell assay to analyze inhibition of forskolin-stimulated cAMP production, 100 nM compound 2 was again able to produce a rightward shift in the DPDPE concentration-response curve (EC50 DPDPE alone: 29 nM±7; EC50 DPDPE+100 nM compound 2: 276 nM±69). Compound 2 produced no inhibition of forskolin-stimulated adenylyl cyclase even at 10 μM (% of forskolin stimulation 91%±6, p>0.05). Again, this ligand displayed a Ke value for antagonism in the nM range (12 nM±3.3).

Peptides DIPP(Ψ)NH$_2$ and Dmt-Tic-Gly-NH-Bzl demonstrated small partial agonism at both MOR and DOR in the

[$^{35}$S]GTPγS assay described above (FIG. 3). Both were characterized further in the adenylyl cyclase inhibition assay, where partial agonism is more readily observed. In addition, both compounds possessed partial agonist efficacies at DOR in this assay as well (FIG. 7B). DIPP(Ψ)NH$_2$ (1 μM) produced 48%±4 inhibition of forskolin-stimulated cAMP at MOR, with an IC50 value of 5.1 nM±3.8. At DOR, DIPP(Ψ)NH$_2$ showed 30%±4 inhibition with an IC50 of 2.2 nM±0.9. Dmt-Tic-Gly-NH-Bzl was less efficacious at both MOR and DOR (35%±10 inhibition at MOR, data not shown and 28%±2 inhibition at DOR), and was less potent at MOR (IC50: 45 nM±13). The IC50 for this peptide at DOR was determined to be 0.7 nM±0.2.

Analgesic Properties of VRP-26

In cell permeability assays, VRP-26 displayed a permeability coefficient ($P_{app}$) of 13.4±7.3×10$^{-6}$ cm/s, which is predictive of a compound that is "well-absorbed" (Arturrson et al., *Biochem Biophys Res Commun.* 199;175(3):880-5). The sensitivity of mice to pain was measured in a nociception assay of tail withdrawal time following a stimulus. Mice injected with saline or vehicle solution exhibited a latency to tail flick of approximately 5 seconds following immersion of the tail tip in warm water. In comparison, animals treated with cumulative doses of VRP-26 administered intraperitoneally exhibited increasing latency up to about 15 seconds after 10 mg/kg VRP-26, demonstrating the analgesic properties of the compound. The percent maximum possible effect averaged across subjects was about 30% after 3 mg/kg VRP-26 and about 70% after 10 mg/kg VRP-26.

Discussion

Compounds 1 and 2 and VRP-26 displayed equivalent binding affinity to MOR and DOR while having lower affinity to KOR (10 to 1000-fold decreased). Compound 2 demonstrated equivalent binding affinity to both MOR and DOR (2.4 nM±0.7 at MOR and 2.3 nM±0.5 at DOR) with a 300-fold decreased affinity to KOR (776 nM±149, FIG. 2). VRP-26 demonstrated equivalent binding affinity to both MOR and DOR (4.7 nM±0.3 at MOR and 4.7 nM±0.1 at DOR) with an almost 200-fold decreased affinity to KOR (810 nM±155, FIG. 4). Additionally, compound 2 and VRP-26 are MOR agonists on par with the clinical standard morphine, providing 59%±11 and 54.4%±6.8, respectively, [$^{35}$S]GTPγS incorporation compared to the 57%±5 afforded by morphine (FIGS. 3, 5, and 6A). Compound 2 behaved on a similar efficacy scale to the endogenous peptide agonist endomorphin-2 (49%±7 [$^{35}$S]GTPγS stimulation compared to 10 μM DAMGO) in this assay as well. Compound 2 peptide was 47 times more potent at G protein stimulation than morphine (p<0.001) and 31 times more potent than endomorphin-2.

Compound 2 also behaved as an antagonist at DOR in the [$^{35}$S]GTPγS assay, able to produce a 26-fold rightward shift in the DPDPE concentration-response curve (FIG. 6B). The calculated Ke value for antagonist potency from this shift was determined to be 4.4 nM±1.4. The G protein stimulation assay requires a high efficacy compound due to the ion and GDP concentrations used. As such, it is possible to classify a compound as an antagonist in this assay when in fact some small partial agonism is unable to be visualized (Purington et al., *J Med Chem* 2009; 52(23):7724-7731). Therefore, a second assay was utilized and examined the inhibition of adenylyl cyclase by a known DOR agonist DPDPE in the presence or absence of compound 2. In this assay, even with downstream signal amplification and decreased efficacy requirements, 10 μM compound 2 was unable to produce significant inhibition of forskolin-stimulated cAMP production (91%±6 forskolin stimulation, or 9% inhibition). A 100 nM concentration of the compound produced a 9.5-fold shift in the EC50 for DPDPE-mediated inhibition (FIG. 7A). This antagonism produced a calculated Ke value of 12 nM±3.3, which is 3-fold greater than the binding affinity of compound 2 in binding to DOR. This relatively small difference in Ke values between the receptor binding and adenylyl cyclase assays may represent differences occurring between cell membrane preparations used for ligand binding and [$^{35}$S]GTPγS incorporation studies and whole cell assays, such as the adenylyl cyclase inhibition assay used here.

DIPP(Ψ)NH$_2$ (Schiller et al., *J Med Chem* 1999; 42(18): 3520-3526) and Dmt-Tic-Gly-NH-Bzl (Balboni et al., *J Med Chem* 2002; 45(3):713-720; and Balboni et al., *Bioorg Med Chem* 2010; 18(16):6024-6030) were both reported to be MOR agonist/DOR antagonist bifunctional pseudopeptides. DIPP(Ψ)NH$_2$ was further characterized as producing less analgesic tolerance than morphine alone (Schiller et al., 1999). In the assays described above, these peptides behaved as low efficacy MOR partial agonists, producing 18%±1 and 7%±2 stimulation at MOR compared to the agonist DAMGO (FIG. 3). Additionally, the peptides were found to be low efficacy agonists at DOR in the adenylyl cyclase inhibition assay, decreasing forskolin stimulation from 100% to 70%±4 (DIPP(Ψ)NH$_2$) and 72%±2 (Dmt-Tic-Gly-NH-Bzl), respectively (FIG. 7B). These peptides also did not display the binding affinity profile desired for these studies (FIG. 2). While DIPP(Ψ)NH$_2$ had equivalent binding affinities to MOR and DOR (0.4 nM±0.1 at MOR and 0.4 nM±0.04 at DOR), it was only 10-fold selective for these receptors over KOR (Ki (KOR): 3.9 nM±0.2) and was found to behave as a partial agonist at KOR as well (11%±3 stimulation). Dmt-Tic-Gly-NH-Bzl, on the other hand, was determined to be DOR-selective, with 0.2 nM±0.06 affinity to DOR and having a 130-fold (26 nM±8) or 640-fold (128 nM±42) decrease in affinity to MOR and KOR, respectively. The differences in binding affinity and efficacy seen in our studies likely reflects differences in assay design from the original reports, and highlights the importance of ion concentrations or other components in determining ligand characteristics.

In summary, compound 2 and VRP-26 were found to be MOR agonist/DOR antagonist bifunctional compounds and displayed equivalent binding affinity to both receptors. At MOR, compound 2 behaved similarly to morphine and endomorphin-2 in in vitro G protein stimulation assays and was more potent than either of those compounds, yet was unable to produce any [$^{35}$S]GTPγS incorporation at DOR. Compound 2 produced a rightward shift in the DPDPE concentration-effect curve in both G protein stimulation and inhibition of adenylyl cyclase assays at DOR, further confirming the antagonist properties of the compound. Characterization of previously published reference ligands DIPP(Ψ)NH$_2$ (Schiller et al., 1999) and Dmt-Tic-Gly-NH-Bzl (Balboni et al., 2002) in these assays demonstrated that compound 2 possessed more desired features for analgesia, including selectivity in binding MOR and DOR over KOR. VRP-26 demonstrated cell penetration in in vitro assays and analgesic properties in in vivo studies.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed:

1. A compound having a structure of formula (I):

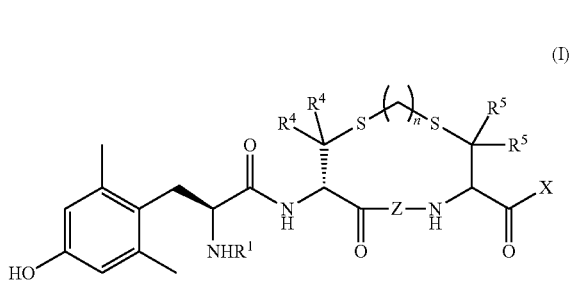

wherein
- $R^1$ is H, C(NH)NH$_2$, an amino acid, or a peptide;
- X is OH, NH$_2$, NHR$^2$, NR$^2$R$^3$, an amino acid, or a peptide;
- $R^2$ and $R^3$ are the same or different and selected from alkyl, alkylenearyl, or alkyleneheteroaryl;
- each $R^4$ and $R^5$ is independently H or CH$_3$;
- Z is an amino acid selected from the group consisting of 2-amino-2,3-dihydro-1H-indene-2-carboxylic acid (Aci); 2-amino-1,2,3,4-tetrahydronaphthalene-2-carboxylic acid (Atc); 6-amino-6,7,8,9-tetrahydro-5H-benzo[7]annulene 6-carboxylic acid; cyclohexylalanine (Cha); cyclohexylglycine (Chg); homophenylalanine (Hfe); 1-naphthylalanine (1-Nal); 2-naphthylalanine (2-Nal); 1,2,3,4-tetrahydroisoquinoline-3-carboxylic acid (Tic); and octahydro-1H-indole-2-carboxylic acid (Oic);
- n is 0, 1, 2, 3, or 4;

with the proviso that X is not NH$_2$ when $R^1$ is H, each $R^4$ is H, each $R^5$ is CH$_3$, Z is Aci, and n is 2;

or a pharmaceutically acceptable salt, ester or solvate thereof.

2. The compound of claim 1, wherein $R^1$ is arginine.

3. The compound of claim 1 or claim 2, wherein X is an amino acid selected from the group consisting of serine, threonine, arginine, homoarginine, and modified residues thereof.

4. The compound of claim 3, wherein X is a modified residue selected from the group consisting of serine, threonine, arginine, and homoarginine, and wherein the modified residue is substituted with one or more of NH$_2$, OH, alkyl substituents, alkylenearyl substituents, alkyloxy substituents, and/or alkylenearyloxy substituents.

5. The compound of claim 4, wherein X is a modified arginine or homoarginine residue having the structure:

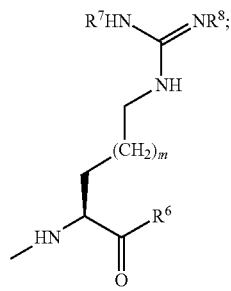

wherein
- m is 1 or 2;
- $R^6$ is selected from the group consisting of NH$_2$, OH, and OR$^9$; and $R^7$, $R^8$, and $R^9$ are individually selected from the group consisting of alkyl substituents and alkylenearyl substituents.

6. The compound of claim 1, wherein $R^1$ and/or X is a glycosylated amino acid or a glycosylated peptide.

7. The compound of claim 1, wherein X is a glycosylated amino acid or glycosylated peptide comprising a glycosyl group selected from the group consisting of alpha and beta anomers of cellobiose, D-glucose, fucose, lactose, maltose, maltotriose, melibiose, and xylose.

8. The compound of claim 1, wherein $R^1$ and/or X is a cell penetrating peptide.

9. The compound of claim 1, wherein each $R^4$ is H.

10. The compound of claim 1, wherein one $R^4$ is H and one $R^4$ is CH$_3$.

11. The compound of claim 1, wherein each $R^4$ is CH$_3$.

12. The compound of claim 1, wherein each $R^5$ is H.

13. The compound of claim 1, wherein one $R^5$ is H and one $R^4$ is CH$_3$.

14. The compound of claim 1, wherein one $R^5$ is H and one $R^5$ is CH$_3$.

15. The compound of claim 1, wherein each $R^5$ is CH$_3$.

16. The compound of claim 1 having a structure:

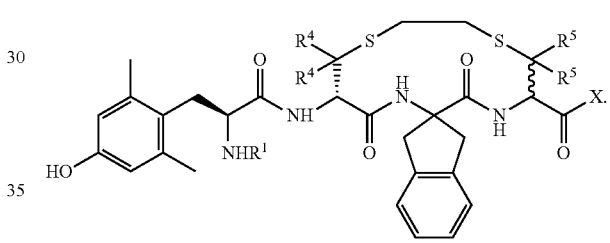

17. The compound of claim 1 having a structure:

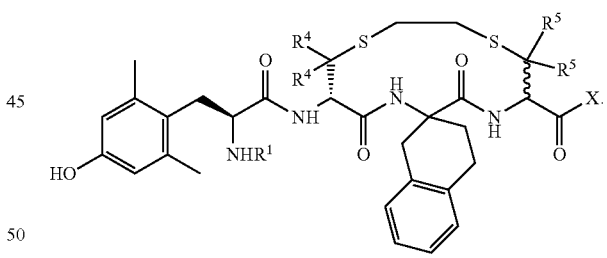

18. The compound of claim 1 having a structure:

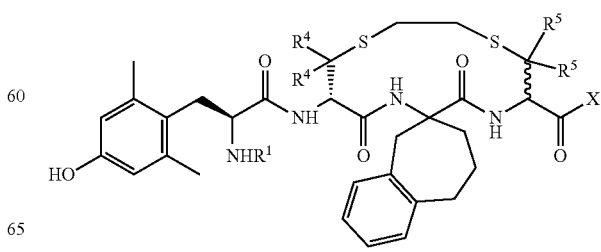

19. The compound of claim 1 having a structure:

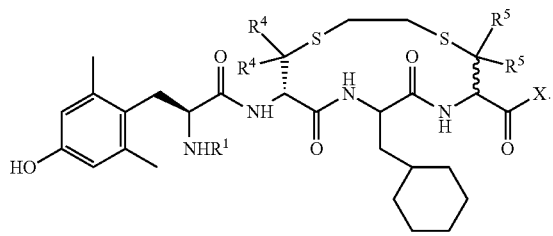

20. The compound of claim 1 having a structure:

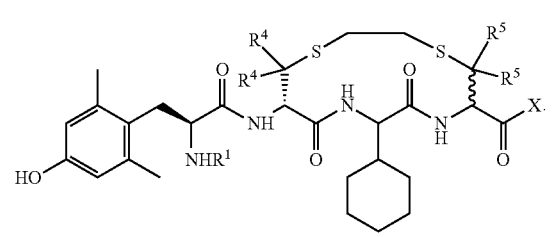

21. The compound of claim 1 having a structure:

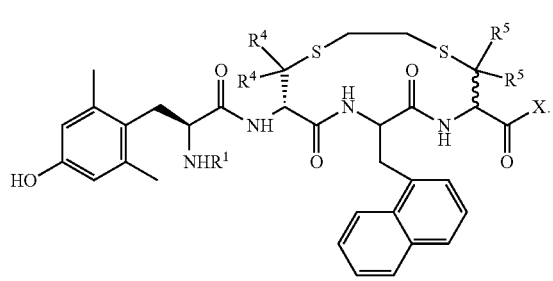

22. The compound of claim 1 having a structure:

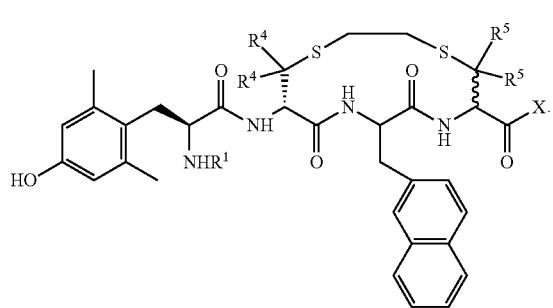

23. The compound of claim 1 having a structure:

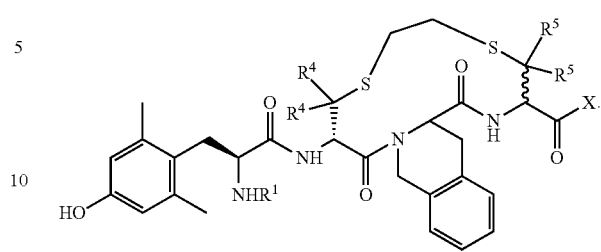

24. The compound of claim 1 having a structure:

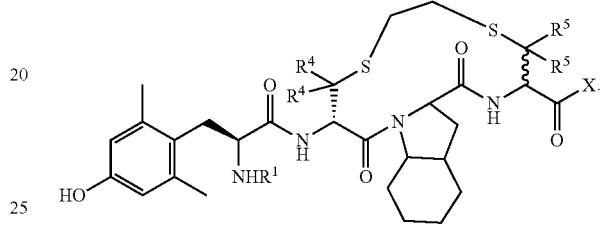

25. The compound of claim 1 having a structure:

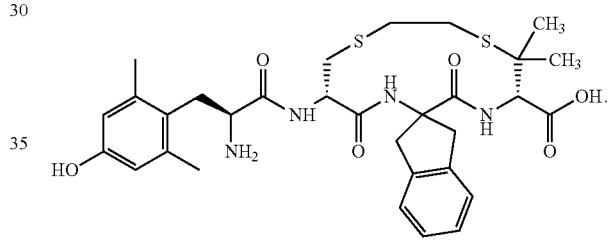

26. The compound of claim 1 having a structure:

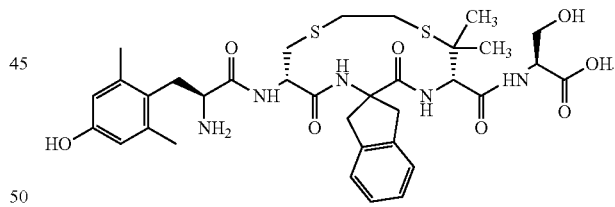

27. The compound of claim 1 having a structure:

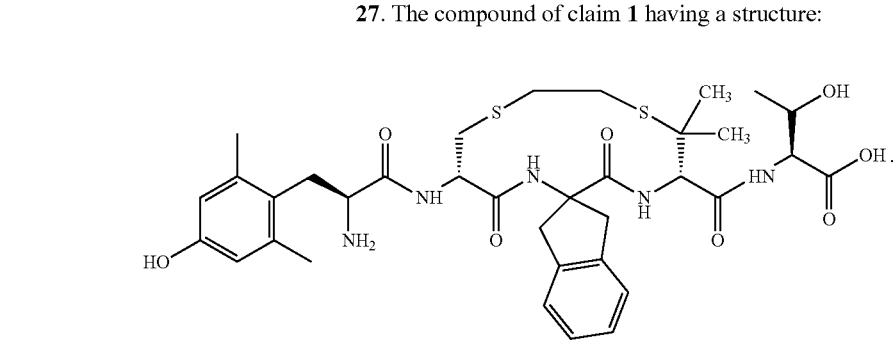

28. The compound of claim 1 having a structure:
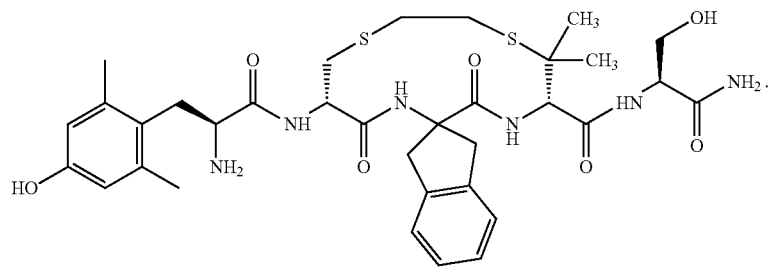 [SMILES: Cc1cc(O)cc(C)c1C[C@H](N)C(=O)N[C@@H]1CSCCSC(C)(C)[C@H](C(=O)N[C@@H](CO)C(N)=O)NC(=O)C2(Cc3ccccc3C2)NC1=O]
29. The compound of claim 1 having a structure:
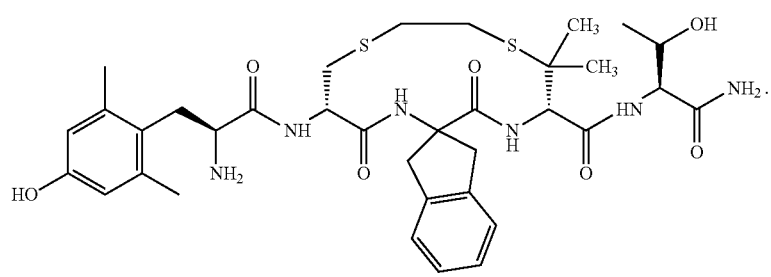 [SMILES: Cc1cc(O)cc(C)c1C[C@H](N)C(=O)N[C@@H]1CSCCSC(C)(C)[C@H](C(=O)N[C@H](C(N)=O)C(C)O)NC(=O)C2(Cc3ccccc3C2)NC1=O]
30. The compound of claim 1 having a structure:
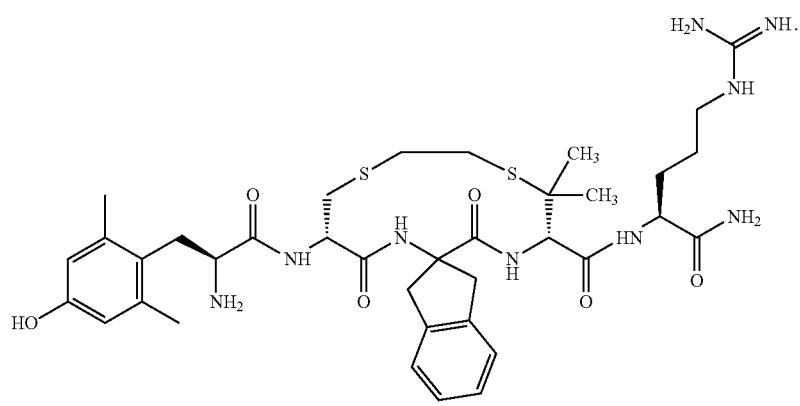 [SMILES: Cc1cc(O)cc(C)c1C[C@H](N)C(=O)N[C@@H]1CSCCSC(C)(C)[C@H](C(=O)N[C@@H](CCCNC(=N)N)C(N)=O)NC(=O)C2(Cc3ccccc3C2)NC1=O]
31. The compound of claim 1 having a structure:
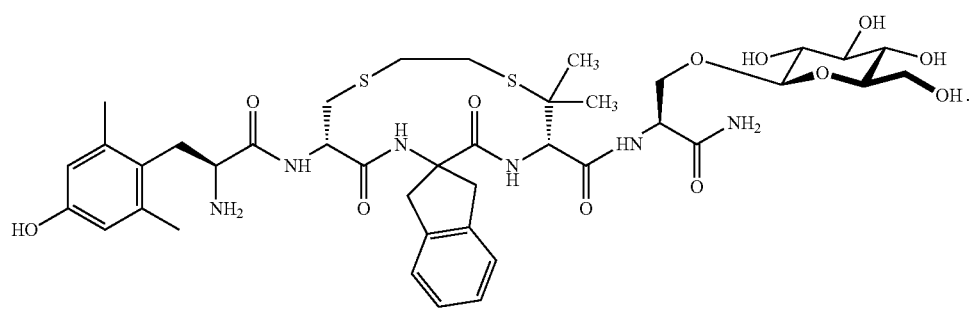

32. The compound of claim 1 conjugated to an entity that enhances the half life of the compound, enhances cellular uptake of the compound, and/or enhances transport across the blood-brain barrier.

33. The compound of claim 32, wherein the compound is conjugated to a water soluble polymer.

34. The compound of claim 32, wherein the compound is conjugated to albumin, an antibody or fragment thereof, or a proline-alanine-serine multimer (PASylation).

35. The compound of claim 1, wherein the compound is a mu-opioid receptor (MOR) agonist and a delta-opioid receptor (DOR) antagonist.

36. The compound of claim 1, wherein the compound displays substantially equivalent binding affinity for MOR and DOR.

37. The compound of claim 1, wherein the compound binds MOR and DOR with an affinity at least 100 times greater than the compound binds kappa-opioid receptor (KOR).

38. A method of modulating the activity of MOR and/or DOR, the method comprising exposing a MOR and/or a DOR to the compound of claim 1.

39. A composition comprising the compound of claim 1 and a pharmaceutically acceptable carrier.

40. The composition of claim 39 further comprising one or more therapeutic agents.

41. A method of treating pain in a subject, the method comprising administering to the subject the composition of claim 39 in an amount sufficient to induce analgesia.

42. The method of claim 41, wherein administration of the composition of claim 39 attenuates physical dependence or tolerance associated with opioid use.

43. A method for treating a mu-opioid receptor (MOR) mediated disorder in a subject, the method comprising administering to the subject the composition of claim 39 in an amount sufficient to ameliorate the disorder.

44. A method for treating a delta-opioid receptor (DOR) mediated disorder in a subject, the method comprising administering to the subject the composition of claim 39 in an amount sufficient to ameliorate the disorder.

45. A method for treating a mu-opioid receptor (MOR) mediated disorder and a delta-opioid receptor (DOR) mediated disorder in a subject, the method comprising administering to the subject the composition of claim 39 in an amount sufficient to ameliorate the disorder.

46. The method of claim 41, wherein the composition is administered intrathecally, intravenously, subcutaneously, intramuscularly, or orally.

47. The method of claim 41, further comprising administering to the subject an additional therapeutic agent and/or an agent that facilitates transport across the blood-brain barrier.

48. A method of modulating the activity of MOR and/or DOR, the method comprising exposing a MOR and/or a DOR to the compound of claim 25.

49. A composition comprising the compound of claim 25 and a pharmaceutically acceptable carrier.

50. The composition of claim 49 further comprising one or more therapeutic agents.

51. A method of treating pain in a subject, the method comprising administering to the subject the composition of claim 49 in an amount sufficient to induce analgesia.

52. The method of claim 51, wherein administration of the composition of claim 49 attenuates physical dependence or tolerance associated with opioid use.

53. A method for treating a mu-opioid receptor (MOR) mediated disorder in a subject, the method comprising administering to the subject the composition of claim 49 in an amount sufficient to ameliorate the disorder.

54. A method for treating a delta-opioid receptor (DOR) mediated disorder in a subject, the method comprising administering to the subject the composition of claim 49 in an amount sufficient to ameliorate the disorder.

55. A method for treating a mu-opioid receptor (MOR) mediated disorder and a delta-opioid receptor (DOR) mediated disorder in a subject, the method comprising administering to the subject the composition of claim 49 in an amount sufficient to ameliorate the disorder.

56. A method of modulating the activity of MOR and/or DOR, the method comprising exposing a MOR and/or a DOR to the compound of claim 31.

57. A composition comprising the compound of claim 31 and a pharmaceutically acceptable carrier.

58. The composition of claim 57 further comprising one or more therapeutic agents.

59. A method of treating pain in a subject, the method comprising administering to the subject the composition of claim 57 in an amount sufficient to induce analgesia.

60. The method of claim 59, wherein administration of the composition of claim 57 attenuates physical dependence or tolerance associated with opioid use.

61. A method for treating a mu-opioid receptor (MOR) mediated disorder in a subject, the method comprising administering to the subject the composition of claim 57 in an amount sufficient to ameliorate the disorder.

62. A method for treating a delta-opioid receptor (DOR) mediated disorder in a subject, the method comprising administering to the subject the composition of claim 57 in an amount sufficient to ameliorate the disorder.

63. A method for treating a mu-opioid receptor (MOR) mediated disorder and a delta-opioid receptor (DOR) mediated disorder in a subject, the method comprising administering to the subject the composition of claim 57 in an amount sufficient to ameliorate the disorder.

* * * * *